US010718750B1

(12) United States Patent
McDaniel

(10) Patent No.: US 10,718,750 B1
(45) Date of Patent: Jul. 21, 2020

(54) LIFE SEEKING EXOPLANET PENETRATOR

(71) Applicant: C. Steven McDaniel, Austin, TX (US)

(72) Inventor: C. Steven McDaniel, Austin, TX (US)

(73) Assignee: Reactive Surfaces Ltd., LLP, Austin, TX (US)

( * ) Notice: Subject to any disclaimer, the term of this patent is extended or adjusted under 35 U.S.C. 154(b) by 709 days.

(21) Appl. No.: 14/979,980

(22) Filed: Dec. 28, 2015

Related U.S. Application Data

(60) Provisional application No. 62/099,174, filed on Jan. 1, 2015.

(51) Int. Cl.
| | | |
|---|---|---|
| *G01N 33/48* | (2006.01) | |
| *B64G 99/00* | (2009.01) | |
| *B64G 1/64* | (2006.01) | |
| *F42B 25/00* | (2006.01) | |
| *G01N 1/04* | (2006.01) | |
| *G01N 35/00* | (2006.01) | |

(52) U.S. Cl.
CPC ............. *G01N 33/48* (2013.01); *B64G 1/641* (2013.01); *B64G 9/00* (2013.01); *F42B 25/00* (2013.01); *G01N 1/04* (2013.01); *G01N 35/0099* (2013.01); *G01N 35/00871* (2013.01)

(58) Field of Classification Search
CPC . E21B 49/02; E21B 49/04; E21B 7/26; E21B 7/007; E21B 7/12; G01V 1/16; B46G 1/105; B46G 2001/1064; B46G 2001/1071
See application file for complete search history.

(56) References Cited

U.S. PATENT DOCUMENTS

| | | | | | |
|---|---|---|---|---|---|
| 3,859,598 | A | * | 1/1975 | McElwain | ................. E21B 7/26 102/400 |
| 4,492,111 | A | * | 1/1985 | Kirkland | .................. G01N 3/48 324/323 |
| 4,726,239 | A | * | 2/1988 | Boggess | ................. E02D 1/025 73/84 |
| 6,097,668 | A | * | 8/2000 | Hopkins | ............... B63B 22/003 367/4 |
| 6,488,105 | B1 | * | 12/2002 | Wilcox | ...................... E21B 4/12 175/19 |
| 7,434,767 | B2 | * | 10/2008 | Smith | ..................... B64G 1/002 244/173.1 |
| 9,115,542 | B1 | * | 8/2015 | Calvert | .................... E21B 7/205 |
| 9,169,695 | B1 | * | 10/2015 | Calvert | ................. E21B 43/116 |
| 9,234,973 | B2 | * | 1/2016 | Scarlatti | ................... G01V 1/16 |
| 9,562,396 | B2 | * | 2/2017 | Baym | ...................... G01V 1/16 |
| 9,726,006 | B2 | * | 8/2017 | Kare | ....................... E21B 47/12 |
| 9,823,070 | B2 | * | 11/2017 | Stephens, Jr. | .......... H04N 7/183 |

(Continued)

OTHER PUBLICATIONS

"MARS-96: Robotic Spacecraft Mission to Mars" http://www.iki.sssi.ru/mars96 (Year: 2003).*

(Continued)

*Primary Examiner* — Joshua T Kennedy
(74) *Attorney, Agent, or Firm* — IVC Patent Agency; David O. Simmons

(57) ABSTRACT

Devices and methods for detection of evidence of life or ore bodies on or near the surface of extraterrestrial bodies (e.g., Mars) are described. In particular, a ground penetrating probe capable of s conducting life detection or other experiments and transmitting the data from the experiments to a satellite relay is described. Methods of use for such devices and apparatus are described.

14 Claims, 6 Drawing Sheets

(56) References Cited

U.S. PATENT DOCUMENTS

| | | | |
|---|---|---|---|
| 9,933,534 B2 * | 4/2018 | Talaalout | G01V 1/166 |
| 2015/0053480 A1 * | 2/2015 | Kare | G01V 1/166 |
| | | | 175/19 |
| 2017/0130531 A1 * | 5/2017 | Russell | E21B 7/007 |

OTHER PUBLICATIONS

"Mars 96 Penetrator" https://nssdc.gsfc.nasa.gov/nmc/spacecraftDisplay.do?id=MARS96D (Year: 2008).*

"MARS Penetrator Umbilical", Christopher Barns, https://ntrs.nasa.gov/archive/nasa/casi.ntrs.nasa.gov/19790013186.pdf (Year: 1979).*

* cited by examiner

LIFE SEEKING EXOPLANET PENETRATOR

This application claims the benefit of U.S. Provisional Application No. 62/099,174, filed Jan. 1, 2015, entitled "LIFE SEEKING EXOPLANET PENETRATOR", incorporated herein in its entirety by reference.

BACKGROUND OF THE INVENTION

1. Field of the Invention

The present invention relates generally to devices and methods for detection of evidence of life on or near the surface of a celestial body such as an extraterrestrial body (e.g., Mars).

2. Description of the Related Art

Various types of unmanned devices such as landers, rovers, and orbiters have been sent to explore extraterrestrial bodies (e.g., a moon, a planet). Unmanned vehicles and probes have been designed for and used in collisions with extraterrestrial bodies including the United States's Ranger 7, 8, and 9 probes and the Lunar Crater Observation and Sensing Satellite; the Union of Soviet Socialist Republics' (U.S.S.R.) Luna 2; the People's Republic of China's Chang'1; the Republic of Indian's Moon Impact Probe directed to the moon. Robotic spacecraft designed for and used to collect and return soil samples from celestial bodies include the U.S.S.R.'s Luna 16, Luna 20 and Luna 24 missions to the moon. Spacecraft designed for soil sampling on Mars included the United States Viking 1 and 2 landers, and the Phoenix Mars Polar Lander, which used experiments designed to detect evidence of life from samples of loose sand several centimeters deep. The Viking landers' data was considered inconclusive as debate continues to whether chemical reactions detected were produced by life or non-living soil chemistry, though some argue that the results support the existence of life (Levin, G. V., "The Labeled Release Experiment—Past and Future" in "Astrobiology and The Search for Life on Mars," Ed. Sarah Kember, ISBN Number 978-1-60785-255-1). Many other landers and probes have been unsuccessfully used, such as the Deep Space 2 probe that lost radio contact upon impact with the Martian surface ("Report on the Loss of the Mars Polar Lander and Deep Space 2 Missions". Jet Propulsion Laboratory. 22 Mar. 2000).

Other unmanned vehicles that can drill surface holes include those by the National Aeronautics and Space Administration (N.A.S.A.), such as the Mars Curiosity rover which can drill a few centimeters/inches into the surface including hard rock and sediment; the Mars Exploration rover which can scratch rock; and the planned InSight lander which is designed to drill 5 meters but not seek life. Unmanned vehicles that are planned to drill and seek life include the ExoMars rover by the European Space Agency, which should be able to drill a couple of meters into the surface. There are presently no such drilling landers that are being sent to seek evidence of living microbes on Mars or any other extraterrestrial body.

SUMMARY OF THE INVENTION

In general, the present invention features a surface penetrating probe for extraterrestrial bodies such as the planet Mars, wherein the surface penetrating probe contains equipment for conducting a life detecting experiment and a communication device to transmit the results of the life detection experiment to a receiver for analysis by a person and/or computer. The surfaces of part (e.g., a scientific equipment package) or all of the penetrating probe are self-cleaning, self-sterilizing, and/or self-decontaminating.

Some embodiments provides a probe for penetrating surface material of a celestial body, comprising, a penetrator, wherein the penetrator comprises: a forward-body section, a mid-body section, and an aft-body section, wherein the forward-body section has a shape and hardened material surface conducive to penetrating the surface of a celestial body between about 0.5 meters to about 10 meters upon an impact speed of about 290 kilometers per hour to about 1450 kilometers per hour, wherein the shape is at least one selected from a screw-like shape, a needle-like shape, a rounded shape, a pointed shape, and a dart-like shape, wherein the hardened material comprises at least one material selected from diamond, tungsten, and tungsten carbide, wherein the mid-body section has a generally cylindrical shape to promote aerodynamic motion of the forward-body section toward a celestial body's surface prior to impact, wherein the aft-body section comprises at least one aerodynamic fin to promote aerodynamic motion of the forward-body section toward a celestial body's surface at an angle between about 90 degrees perpendicular to about 45 degrees to the celestial body's surface prior to impact to promote penetration upon impact with the celestial body's surface, wherein the aft-body section separates from the mid-body section upon penetration of the mid-body section into the surface of the celestial body due to the aerodynamic fin impeding penetration of the aft-body section upon contact with the surface of the celestial body so part or all of the aft-body section is located above, at or near the surface of the celestial body upon the end of impact driven forward motion after contact with the surface of the celestial body, and wherein the length of the penetrator prior to contact with the surface of the celestial body is between about 0.15 meters to about 6 meters; an equipment payload, wherein the equipment payload is housed within at least one of the forward-body section, the mid-body section, and the aft-body section, wherein the equipment payload comprises, an impact damper to reduce impact damage to other parts of the equipment payload, wherein the impact damper is at least one selected from an air-bag device, a spring, and a shock absorber, a scientific equipment package, wherein the scientific equipment package comprises, at least one piece of scientific equipment, wherein the at least one piece of scientific equipment is capable of conducting a life detection experiment, a sampling device, wherein the sampling device is capable of obtaining material of the celestial body located at a depth of at least 1 meter beneath the surface of the celestial body and moving the material to the piece of scientific equipment to undergo a life detection experiment, and wherein the sampling device accesses the material of the celestial body through the opening in the housing of the penetrator between the mid-body section and the aft-body section created by the separation of those sections after impact with the celestial body's surface; an antimicrobial and anti-nucleic acid coating, wherein the antimicrobial and anti-nucleic acid coating is applied to internal surface of the penetrator to promote biological sterility and reduce nucleic acid contamination prior to conducting the life detection experiment to improve data quality of the life detection experiment, a communication device operatively connected to the piece of scientific equipment to electromagnetically transmit the results of the life detection experiment, wherein the communication device comprises, a radio transmitter, an antenna capable of electromagnetically transmitting the results of the life detection experiment, wherein the antenna is operatively associated with the aft-body section so the antenna is located above, at or near the surface of the celestial body upon rest after contact with the surface of the celestial body to promote transmission of the results of the life detection experiment, the umbilical wire connecting the mid-body section to the aft-body section, wherein the umbilical wire is operatively associated with the at least one of the scientific equipment package and the antenna; a microprocessor operatively associated with at least one of the scientific equipment package and the communication device; an electrical power system operatively associated with at least one of the scientific equipment package, the communication device, and the microprocessor, wherein the power system comprises a battery; and wherein the penetrator is operatively associated with a spacecraft, wherein the spacecraft positions the penetrator above the surface material of celestial body and then the penetrator is released so to impact the surface material of the celestial body and penetrate about 1 meter to about 10 meters deep in the celestial body to allow the sampling device to obtain material of the celestial body from at least 1 meter below the surface of the celestial body prior to conducting a life detection experiment.

In some aspects, the communication package electromagnetically transmit the results of the life detection experiment to a communication network, wherein the communication network comprises at least one selected from a ground based relay, an atmosphere borne relay, a space based relay, and an Earth based satellite dish, wherein the ground based relay comprises at least one selected from a lander and another penetrator, wherein the atmosphere borne relay comprises at least one selected from a balloon, a drone, and a sub-orbital craft, and wherein the a space based relay comprises at least one selected from a satellite, and an orbiting spacecraft.

In other aspects, the scientific equipment package comprises at least one additional piece of equipment capable of conducting at least one experiment selected from life detection, seismometry, thermal measurement, and geodesy.

In further aspects, the communication device comprises a plurality of communication devices.

In some aspects, the electrical power system further comprises at least one of a solar panel, a thermoelectric generator, and a windmill.

In additional aspects, the penetrator comprises a depth achievement device, wherein the depth achievement device comprises at least one explosive charge operatively associated with the forward body section of the penetrator that detonates upon or after impact of the penetrator with the celestial body's surface, a drill operatively associated with the forward body section of the penetrator, another penetrator that impacts the same location of the surface of the celestial body prior to impact of the penetrator, and a bomb that impacts and detonates at the same location of the surface of the celestial body prior to impact of the penetrator.

In other aspects, the penetrator further comprises an outer aeroshell to protect the penetrator during atmospheric entry.

In specific aspects, the penetrator comprises an engine, wherein the engine comprises at least one selected from a rocket engine and a jet engine, wherein the engine begins to function at or after release from the spacecraft to move the penetrator to a selected area of surface material of the celestial body to impact, to prevent impact of the penetrator with the surface material of a celestial body at a speed below about 290 kilometers per hour, to function as a depth achievement device at or after impact, or a combination thereof.

In particular aspects, the penetrator comprises a descent speed control device to prevent impact of the penetrator with the surface material of a celestial body at a speed in excess of about 1450 kilometers per hour, wherein the descent speed control device comprises at least one selected from a parachute, a rocket engine, and a jet engine.

In further aspects, the surface material of the celestial body impacted by the penetrator probe is at least one selected from a lava tube, a cave, a karst, a crater gully, a steep inclined area, and an area suspected or known to have a subsurface deposit of at least one selected from water, oil, a mineral, and an ore.

In certain aspects, the penetrator is a plurality of penetrators. In some facets, the plurality of penetrators are designed to impact different locations of surface material of the celestial body, wherein at least one penetrator of the plurality of penetrators comprise at least one of a different shape, different hardened material, and different depth achievement device, and different impact damper relative to another penetrator of the plurality of penetrators.

Certain embodiments provide a scientific probe for penetrating surface material of a celestial body with a penetrator, wherein the penetrator comprises: a forward-body section, a mid-body section, and an aft-body section, wherein the forward-body section has a shape and hardened material surface conducive to penetrating the surface of a celestial body between about 0.5 meters to about 10 meters upon an impact speed of about 290 kilometers per hour to about 1450 kilometers per hour, wherein the shape is at least one selected from a screw-like shape, a needle-like shape, a rounded shape, a pointed shape, and a dart-like shape, wherein the hardened material comprises at least one material selected from diamond, tungsten, and tungsten carbide, wherein the mid-body section has a generally cylindrical shape to promote aerodynamic motion of the forward-body section toward a celestial body's surface prior to impact, wherein the aft-body section comprises at least one aerodynamic fin to promote aerodynamic motion of the forward-body section toward a celestial body's surface prior to impact, and wherein the length of the penetrator prior to contact with the surface of the celestial body is between about 0.15 meters to about 6 meters; an equipment payload, wherein the equipment payload is housed within at least one of the forward-body section, the mid-body section, and the aft-body section, wherein the equipment payload comprises, a scientific equipment package, wherein the scientific equipment package comprises, at least one piece of scientific equipment, wherein the at least one piece of scientific equipment is capable of conducting a life detection experiment, a sampling device, wherein the sampling device is capable of obtaining material of the celestial body and moving the material to the piece of scientific equipment to undergo a life detection experiment; an impact damper to reduce impact damage to other parts of the equipment payload, wherein the impact damper is at least one selected from an air-bag device, a spring, and a shock absorber, a communication device operatively connected to the piece of scientific equipment to electromagnetically transmit the results of the life detection experiment, wherein the communication device comprises, a radio transmitter, an antenna capable of electromagnetically transmitting the results of the life detection experiment, the umbilical wire connecting the mid-body section to the aft-body section, wherein the umbilical wire is operatively associated with the at least one of the scientific equipment package and the antenna; a microprocessor operatively associated with at least one of the scientific equipment package and the communication device; an electrical power system operatively associated with at least one of the scientific equipment package, the communication device, and the microprocessor, wherein the power system comprises a battery; and wherein the penetrator is operatively associated with a spacecraft, wherein the spacecraft positions the penetrator above the surface material of celestial body and then the penetrator is released so to impact the surface material of the celestial body, wherein the improvement comprises an antimicrobial and anti-nucleic acid coating, wherein the antimicrobial and anti-nucleic acid coating is applied to internal surface of the penetrator to promote biological sterility and reduce nucleic acid contamination prior to conducting the life detection experiment to improve data quality of the life detection experiment, the penetrator penetrates about 1 meter to about 10 meters deep in a celestial body to allow the sampling device to obtain material of the celestial body from at least 1 meter below the surface of the celestial body prior to conducting a life detection experiment, wherein the antenna is operatively associated with the aft-body section, and wherein the aft-body section separates from the mid-body section upon penetration of the mid-body section into the surface of the celestial body due to the aerodynamic fin impeding penetration of the aft-body section upon contact with the surface of the celestial body so the antenna is located above, at or near the surface of the celestial body upon rest after contact with the surface of the celestial body to promote transmission of the results of the life detection experiment.

Other embodiments provide a method for penetrating surface material of a celestial body, comprising: assembling a penetrator that comprises a forward-body section, a mid-body section, and an aft-body section, wherein the forward-body section has a shape and hardened material surface conducive to penetrating the surface of a celestial body between about 0.5 meters to about 10 meters upon an impact speed of about 290 kilometers per hour to about 1450 kilometers per hour, wherein the shape is at least one selected from a screw-like shape, a needle-like shape, a rounded shape, a pointed shape, and a dart-like shape, wherein the hardened material comprises at least one material selected from diamond, tungsten, and tungsten carbide, wherein the mid-body section has a generally cylindrical shape to promote aerodynamic motion of the forward-body section toward a celestial body's surface prior to impact, wherein the aft-body section comprises at least one aerodynamic fin to promote aerodynamic motion of the forward-body section toward a celestial body's surface at an angle between about 90 degrees perpendicular to about 45 degrees to the celestial body's surface prior to impact to promote penetration upon impact with the celestial body's surface, wherein the aft-body section separates from the mid-body section upon penetration of the mid-body section into the surface of the celestial body due to the aerodynamic fin impeding penetration of the aft-body section upon contact with the surface of the celestial body so part or all of the aft-body section is located above, at or near the surface of the celestial body upon the end of impact driven forward motion after contact with the surface of the celestial body, and wherein the length of the penetrator prior to contact with the surface of the celestial body is between about 0.15 meters to about 6 meters; incorporating into the penetrator an equipment payload, wherein the equipment payload is housed within at least one of the forward-body section, the mid-body section, and the aft-body section, wherein the equipment payload comprises, an impact damper to reduce impact damage to other parts of the equipment payload, wherein the impact damper is at least one selected from an air-bag device, a spring, and a shock absorber, a scientific equipment package, wherein the scientific equipment package comprises, at least one piece of scientific equipment, wherein the at least one piece of scientific equipment is capable of conducting a life detection experiment, a sampling device, wherein the sampling device is capable of obtaining material of the celestial body located at a depth of at least 1 meter beneath the surface of the celestial body and moving the material to the piece of scientific equipment to undergo a life detection experiment, and wherein the sampling device accesses the material of the celestial body through the opening in the housing of the penetrator between the mid-body section and the aft-body section created by the separation of those sections after impact with the celestial body's surface; an antimicrobial and anti-nucleic acid coating, wherein the antimicrobial and anti-nucleic acid coating is applied to internal surface of the penetrator to promote biological sterility and reduce nucleic acid contamination prior to conducting the life detection experiment to improve data quality of the life detection experiment, a communication device operatively connected to the piece of scientific equipment to electromagnetically transmit the results of the life detection experiment, wherein the communication device comprises, a radio transmitter, an antenna capable of electromagnetically transmitting the results of the life detection experiment, wherein the antenna is operatively associated with the aft-body section so the antenna is located above, at or near the surface of the celestial body upon rest after contact with the surface of the celestial body to promote transmission of the results of the life detection experiment, the umbilical wire connecting the mid-body section to the aft-body section, wherein the umbilical wire is operatively associated with the at least one of the scientific equipment package and the antenna; a microprocessor operatively associated with at least one of the scientific equipment package and the communication device; an electrical power system operatively associated with at least one of the scientific equipment package, the communication device, and the microprocessor, wherein the power system comprises a battery; and wherein the penetrator is operatively associated with a spacecraft, wherein the spacecraft positions the penetrator above the surface material of celestial body and then the penetrator is released so to impact the surface material of the celestial body and penetrate about 1 meter to about 10 meters deep in the celestial body to allow the sampling device to obtain material of the celestial body from at least 1 meter below the surface of the celestial body prior to conducting a life detection experiment.

DETAILED DESCRIPTION OF THE EMBODIMENTS

Figure 1:
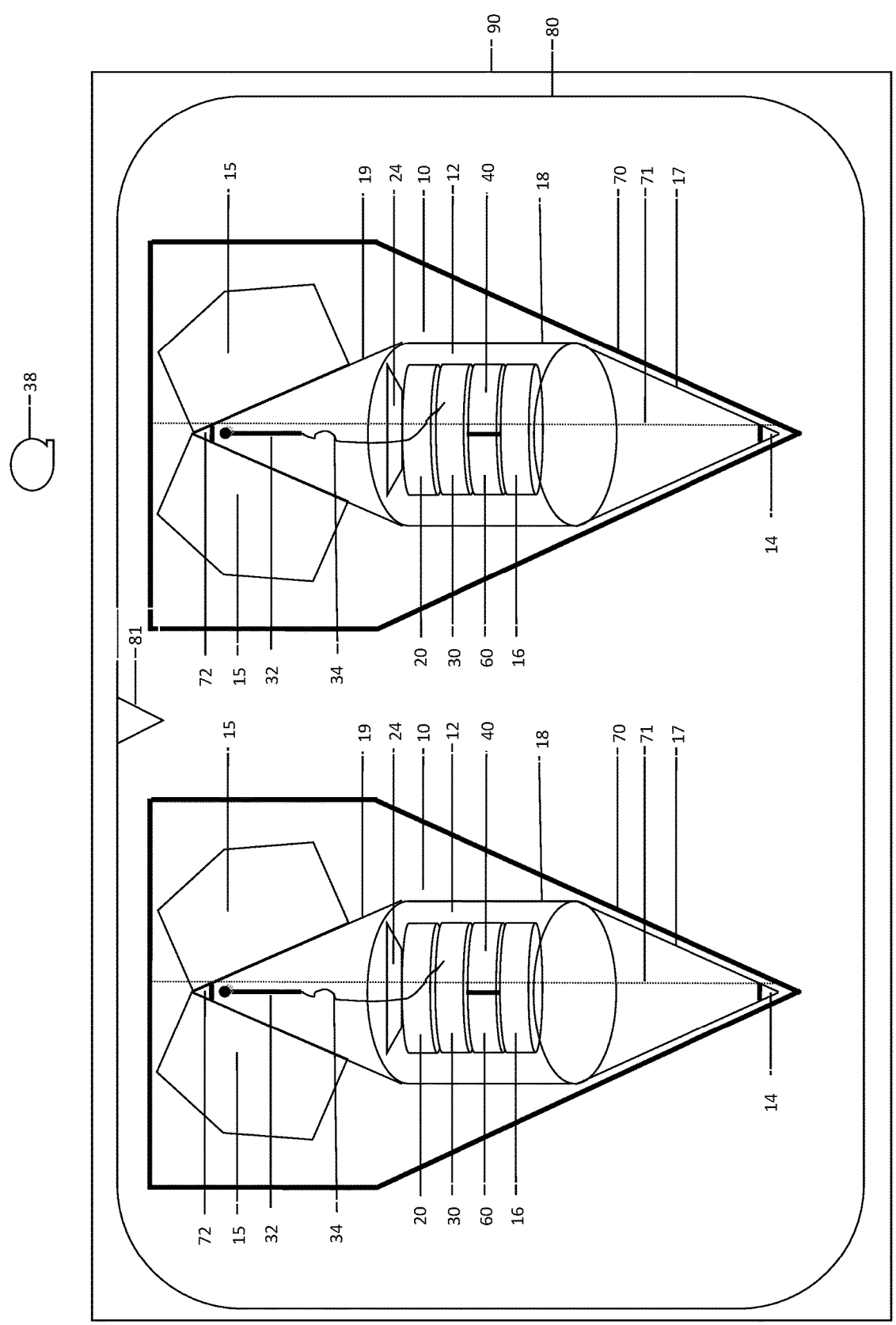
FIG. 1 depicts a plurality of penetrators contained within a quiver that is contained within a spacecraft.

For further understanding of the embodiments of the invention, reference is made to the following detailed description, taken in conjunction with the accompanying drawing(s) in which reference character(s) designate like or similar element(s) throughout the several figures of the drawing(s). It will appreciated that various adaptation(s), change(s), equivalent(s), modification(s), substitution(s), deletion(s), and/or addition(s) of material(s), procedure(s) and/or protocol(s) may be made without departing from the spirit and scope of the invention. It is to be understood, however, that the present invention may be embodied in various form(s). Therefore, specific detail(s) disclosed herein are not to be interpreted as limiting, but rather as a basis for the claim(s) and as a representative basis for teaching the embodiment(s) in virtually any appropriately detailed system, structure or manner.

As used herein other than the claims, the terms "a," "an," "the," and/or "said" means one or more. As used herein in the claim(s), when used in conjunction with the word(s) "comprise," "comprises" and/or "comprising," the word(s) "a," "an," "the," and/or "said" may mean one or more than one. As used herein and in the claim(s), the terms "having," "has," "is," "have," "including," "includes," and/or "include" has the same meaning as "comprising," "comprises," and "comprise." As used herein and in the claims "another" may mean at least a second or more. As used herein and in the claim(s), "about" refers to any inherent measurement error or a rounding of digit(s) for a value (e.g., a measured value, calculated value such as a ratio), and thus the term "about" may be used with any value and/or range. The phrase "a combination thereof" "a mixture thereof" following a listing, the use of "and/or" as part of a listing, a listing in a table, the use of "etc" as part of a listing, the phrase "such as," and/or a listing within brackets with "e.g.," or "i.e.," refers to any combination (e.g., any sub-set) of a set of listed component(s), and combination(s) and/or mixture(s) of related specie(s) and/or embodiment(s) described herein though not directly placed in such a listing are also contemplated. For example, component(s) such as valve(s) described in different section(s) of the specification may be claimed individually and/or as a combination, as they are part of the same genera. Such related and/or like genera(s), sub-genera(s), specie(s), and/or embodiment(s) described herein are contemplated both in the form of an individual component that may be claimed, as well as a mixture and/or a combination that may be described in the claim(s) as "at least one selected from," "a mixture thereof" and/or "a combination thereof." Term(s) such as "such as" and/or "e.g.," generally refer to non-limiting example(s).

It will be understood herein that a given range includes all integers and sub-ranges comprised within the cited range. For example, citation of a range "0.03% to 0.07%" refers to specific values and sub-ranges within the cited range, such as, for example, 0.03%, 0.04%, 0.05%, 0.06%, and 0.07%, as well as various combinations of such specific values, such as, for example, 0.03%, 0.06% and 0.07%, 0.04% and 0.06%, or 0.05% and 0.07%, as well as sub-ranges such as 0.03% to 0.05%, 0.04% to 0.07%, or 0.04% to 0.06%, etc. Examples of specific values that can be within a cited range include 0.000001, 0.00001, 0.0001, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1050, 1100, 1150, 1200, 1250, 1300, 1350, 1400, 1450, 1500, 1600, 1700, 1800, 1900, 2000, 3000, 4000, 5000, 6000, 7000, 8000, 9000, 10,000, 100,000, 1,000,000 or more.

All patents and publications mentioned in this specification are herein incorporated by reference to the same extent as if each individual publication was specifically and individually indicated to be incorporated by reference. In particular, U.S. Pat. Nos. 4,909,460, 6,105,695, 6,112,843, 6,488,306, 8,159,357, and 8,608,113; as well as "*CubeSat Design Specification Rev.* 13 Updated 6-6-2015" California State Polytechnic University, "NPS CubeSat Launcher Design, Process And Requirements" by Matthew Richard Crook, Naval Post Graduate School, Monterey, Calif., June 2009, "Deployable Helical Antenna for Nano-Satellite" by Daniel Ochoa, Northrop Grumman Aerospace Systems, 2014, "Elements of Spacecraft Design by Charles D. Brown, American Institute of Aeronautics and Astronautics, Incorporated, 2002, and Space Vehicle Design by Michael Douglas Griffin and James R. French, American Institute of Aeronautics and Astronautics, Incorporated, 2004, are incorporated herein by reference in their entirety as exemplary materials and components in the art that may be used in the apparatus, devices, methods, and compositions disclosed herein.

System(s) and method(s) are provided for a delivery system comprising a penetrator from sub-orbital to orbital height impacts onto a surface ("crust") of a celestial body such as an asteroid, a comet, a moon, a planetoid, a planet, a terrestrial body (i.e., Earth), an extraterrestrial body (e.g., Mars), etc. In other embodiments, it is contemplated that a penetrator may be designed for reduced weight and/or size to allow reduced production cost and/or ease of transport by the space craft given that that many spacecraft are limited in size and weight for ease of interplanetary travel (e.g., reduced fuel consumption).

FIG. 1 depict two exemplary penetrators 10 ("penetrator probe," "penetrating device," "arrow," "dart," "needle") each encased by an optional outer aeroshell 70. The aeroshell 70 generally will split along a seam 71 into 2 or more pieces that detach prior to impact of penetrator(s) with the celestial body's surface. It is contemplated that one or more penetrator(s) 10 may reach ("be delivered") by a spacecraft 90, and typically is attached to the spacecraft via a separate compartment referred to herein as a quiver 80.

The spacecraft 90 carries the penetrator(s) 10 to orbital or suborbital heights relative to a celestial body. The quiver 80 and/or the penetrator 10 may be carried ("piggyback") to a celestial body by another spacecraft (e.g., a spacecraft from N.A.S.A., E.S.A., a commercial spacecraft, etc.) designed for other functions than use with a penetrator 10, such as for example, a future mission (e.g., the 2016 Insight mission; the 2018 ExoMars mission, the N.A.S.A. Mars 2020 mission).

The penetrators 10 generally comprise an equipment payload 12. In some embodiments the equipment payload 12 typically comprises an impact damper (e.g., air-bag devices, cushioning materials, springs, shock absorber, etc.) 16 to reduce impact damage to other parts of the equipment payload 12; a scientific equipment package ("scientific equipment," "sensor equipment," "scientific payload") 20 for conducting scientific experiment(s) (e.g., a life detection device/experiment); a communication device ("communication package," "communication equipment," "communication link," "information transmission device") 30 for conveying information from the penetrator to a separate communication relay network ("communication network") 38; a microprocessor ("computer") 40 for controlling and processing information to and from the other various components of the penetrator 10; a power system 60 for providing energy (e.g., electricity, heat, light, etc.) to other components of the penetrator 10; or a combination thereof.

In some embodiments all or part of the scientific equipment package 20 deploy beyond the outer surface of the penetrator 10 to conduct scientific experiments including life detection experiment(s). In certain aspects, a scientific equipment package 20 may comprise one or more celestial body sampling device(s) 24 such as a passive collection device (e.g., a funnel, a permeable grill, etc.) that becomes open to the environment outside the penetrator 10 after impact to capture loose surface material (whether the loose material was present before impact of the penetrator 10 or loosened by one or more components of the penetrator 10 upon contact with the celestial body i.e., a hole 101 having loosened surface material) of the celestial body's surface a robot (e.g., microbot rover(s), arm(s), drill(s), pincer(s)), etc.) that collects sample(s) of surface material (e.g., soil, dirt, rocks, etc.) from the celestial body or a combination thereof. In specific facets, the sampling device 24 obtains ("collects") celestial body surface material outside the penetrator 10 and moves the material to a piece of scientific equipment 20 capable of conducting a scientific experiment (e.g., life detection experiments).

In some facets, the power system 60 comprises a battery, a solar panel, a thermoelectric generator, a fuel cell, a windmill, or a combination thereof.

In other facets, the microprocessor 40 may comprise an electronic memory storage to operate one or more of any device or part (e.g., the scientific equipment package 20, the communication device 30, the quiver 80, etc.) of the penetrator 10.

In other embodiments, the communication device 30 and/or the communication network 38 comprises a radio transmitter; a radio receiver; a laser based communication signaling device, or other types of device(s) and/or apparatus(s) known in the art for electromagnetic, electronic, and/or electrical information transmission. A communication device 30 may be used to convey information such as scientific data collected by one part of a penetrator 10 (e.g., a scientific equipment package 20) and/or operation instructions (e.g., preprogramed instructions in the microprocessor 40, instructions from another penetrator 10, instructions from the communication network 38) between different part(s) and/or section(s) the penetrator 10; a communication network 38; another penetrator(s) 10; or a combination thereof. In some aspects, the communication device 30 further comprises an antenna ("communication antenna," "aerial") 32 that may be deployable or stationary, and optionally an umbilical wire ("umbilical," "tether") 34 connecting part of the communication device 30 to another part of the communication device (e.g., the antenna 32) and/or a part of the penetrator (e.g., a part of the equipment package 10 such as the scientific equipment package 20). In specific facets, the penetrator comprises a plurality of communication device(s) 30 to foster such information transmission, such as by short distance radio transmission to various part(s) of the penetrator 10 and/or the communication network 38.

In specific aspects, the penetrator 10 may comprise different body sections, such as for example, a forward-body section 17, a mid-body section ("mid-section") 18, an aft-body section ("aft-section, "tail section") 19, or a combination thereof. In some facets, one or more section(s) of the penetrator 10 have a different shape that is different than another section(s) of the penetrator [e.g., a forward-body section 17 having a screw like shape (not shown) to promote burrowing]. For example, the forward-body section may have a conical shape to promote penetration upon contact with the celestial body(s) surface while the mid-body section 18 may a cylindrical shape to promote aerodynamic motion of the forward-body section 17 toward the celestial body's surface prior to impact. In specific facets, one or more of the forward-body section 17, the mid-body section 18, or the aft-body section 19 comprises (e.g., houses, contains) all or part of the equipment payload 12. In some facets, the aft-body section 19 comprises all or part of the communication device 30 (e.g., an antenna 32), such as to foster communication with the communication network 38 and/or other penetrator(s) 10. In some aspects, one or more of the sections (e.g., the aft-body section) of the penetrator 10 have one or more aerodynamic fin(s) 15 to foster forward-body section 17 direction toward the surface, imped non-perpendicular penetration of the penetrator 10 into the celestial body's surface, and/or depending upon aerodynamic design enhance or imped rotation, depending upon the desired aerodynamic and/or penetration (e.g., screw-like motion) properties, of the penetrator 10 during decent through an atmosphere.

In some aspects, to reach a depth desired for operation of the equipment payload 12, a penetrator 10 may comprise: a depth achievement device 14. In some aspects, the depth achievement 14 device may comprise an explosive charge; a drill; a penetration aid feature such as a penetration promoting shape (e.g., a rounded shape, a pointed shape, a screw-like shape, a needle-like shape, a dart-like shape, etc.) such as those produced by aeronautical engineering, a hardened surface (e.g., diamond, tungsten, tungsten based alloys such as tungsten carbide, etc.), and/or a dense material (e.g., uranium, depleted uranium, uranium alloys, osmium, etc.) (Cai et al., *Rev. Particulate Mater.* 3: 71-131, 1995) at or near the likely area(s) of the penetrator that will first contact the celestial body's solid surface; or a combination thereof. In many embodiments the penetrator 10 may have the material construction and/or design to produce penetration capability when piercing a surface material (e.g., soil, dirt, pebbles, gravel, carbon dioxide ice, water ice, etc.) similar to or the same as a military type "bunker-buster" bomb (e.g., "penetrating round") and/or missile. For example, to achieve enhanced depth, a penetrator 10 may initially bury about 2 meters due to impact forces, but the function of the depth achievement device 14 (e.g., a drill) may obtain a total depth of about 5 meters (about 16.4 feet). This would allow deployment of part or all of the equipment payload 12 at a particular depth within the span of 5 meters (e.g., a target depth for deployment of the equipment payload 12 at about 4 meters (about 13.1 feet) deep could then be achieved). In another example of enhance depth achievement, a hole 101 is produced in the surface of the celestial body by the depth achievement device 14 (e.g., a bomb, another penetrator device) prior to contact with the rest of the penetrator 10 which increases the hole's 101 total depth due to impact forces. In a further example of selected depth achievement, the depth achievement device 14 (e.g., friction producing materials and/or shapes on the penetrator 10) may limit the depth produced by ballistic penetration to avoid surface material penetration beyond a desired depth.

The length of the penetrator 10 may vary depending upon the equipment payload's 12 size and the desired depth to be achieved, but generally in many embodiments the penetrator's 10 length is between about 0.15 meters (e.g., about 6 inches) to about 6 meters (e.g., about 20 feet). In general aspects, the penetrator 10 is capable of function in a celestial environment (e.g., temperature, pressure, wind, dust, radiation, etc.) and/or a buried/underground environment, depending upon how much surface material such as loose dirt, gravel, carbon dioxide ice, water ice, etc. covers the equipment payload 12 after contacting (e.g., impacting) the celestial body (e.g., contacting the surface, contacting the atmosphere).

In many embodiments, the quiver 80 comprises an atmospheric entry speed control device 81. In other aspects, the penetrator 10 and/or the outer aeroshell 70 comprise a descent speed control device 72 (not shown for the outer aeroshell 70). The atmospheric entry speed control device 81 and the descent speed control device 72 generally comprise components known in the art to increase and/or decrease the speed of an apparatus such as a penetrator 10 in an atmosphere to maintain a desired speed, control the penetration angle of the penetrator 10 relative to the celestial body's surface, and/or create a speed differential between component(s), such as an penetrator 10 falling away from a quiver 80 being slowed by an atmospheric speed control device 81. In general embodiments, an atmospheric entry control device 81 and/or a descent speed control device will comprise at least one selected from a parachute (e.g., a deployable parachute, a releasable parachute), a rocket engine, and a jet engine. In other aspects, an atmospheric entry control device 81 and/or a descent speed control device 72 modulates the decent speed of the penetrator 10 to a desired speed, particularly the desired speed of impact with a celestial body's surface. In some facets, the penetrator 10 impacts a surface between about 290 kilometers per hour (about 180 miles per hour) to about 1450 kilometers per hour (about 900 miles per hour).

Figure 2:
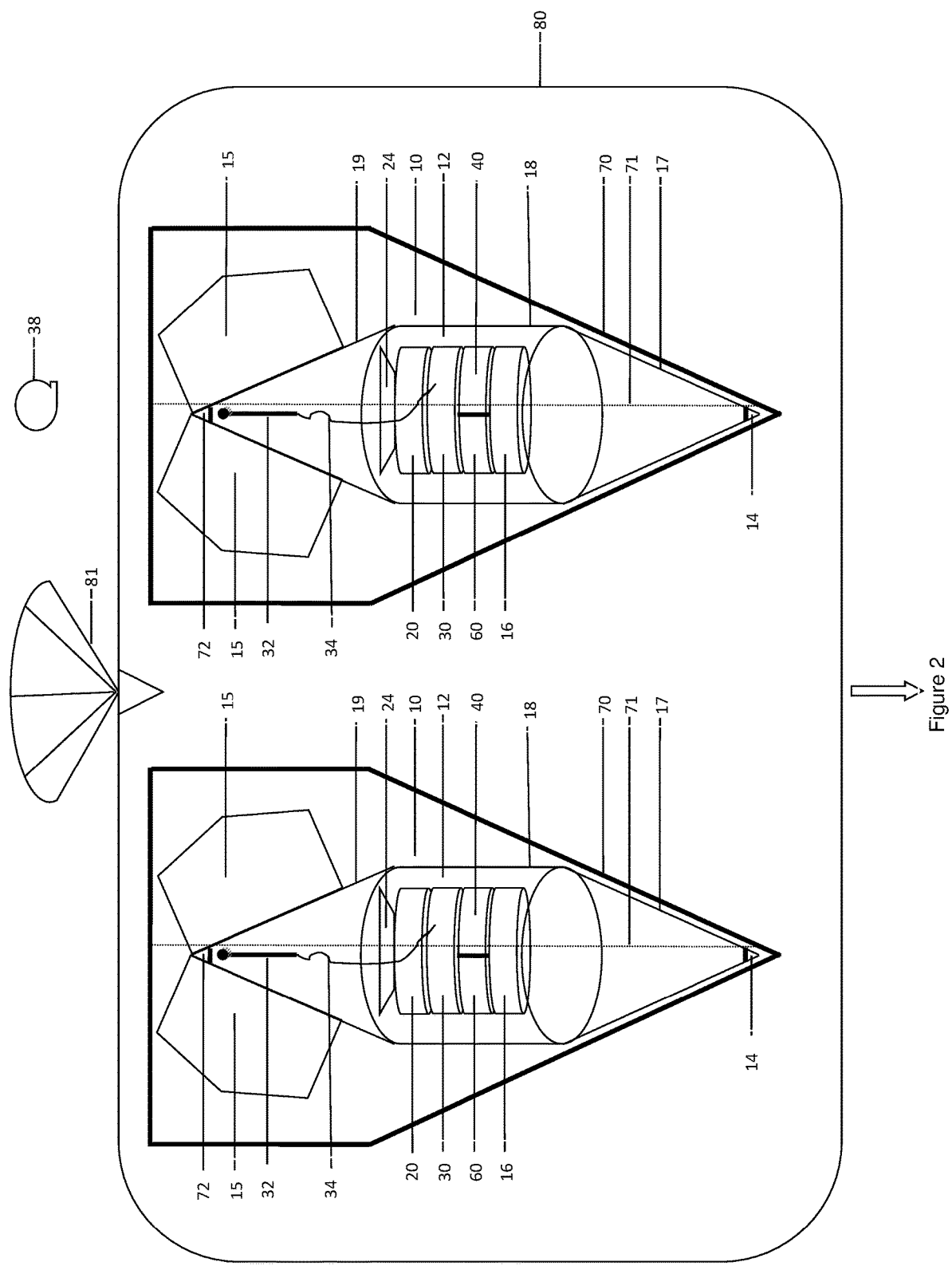
FIG. 2 depicts the penetrators within the quiver after release from the spacecraft, with motion toward a celestial body indicated by an arrow(s).

FIG. 2 shows the quiver 80 after being released from the spacecraft 90. As used herein "released" may include simple detachment (e.g., opening of latches securing the quiver 80 to the spacecraft 90; wind shear causing components to separate from each other, etc.) that allows gravity driven ("drop," "fall,") ballistic impact with the surface of the celestial body; and/or excess velocity/kinetic energy from space travel to supplement ballistic impact with the surface of the celestial body; and/or acceleration ("shooting," "shot," "expel") such as by a rocket, magnetic (e.g., rail gun) driven movement, explosion driven release (e.g., via explosive bolt(s)), gas expansion due to pressure differences by opening of a pressurized compartment containing the penetrator 10 and/or quiver 80; or a combination thereof. For example, a spacecraft 90 typically uses releasable ballast, and a quiver 80 and/or penetrator 10 could also function as part or all of the ballast. The atmospheric speed control device 81, depicted as a parachute, has been deployed to modulate speed of the quiver 80 through the atmosphere.

Figure 3:
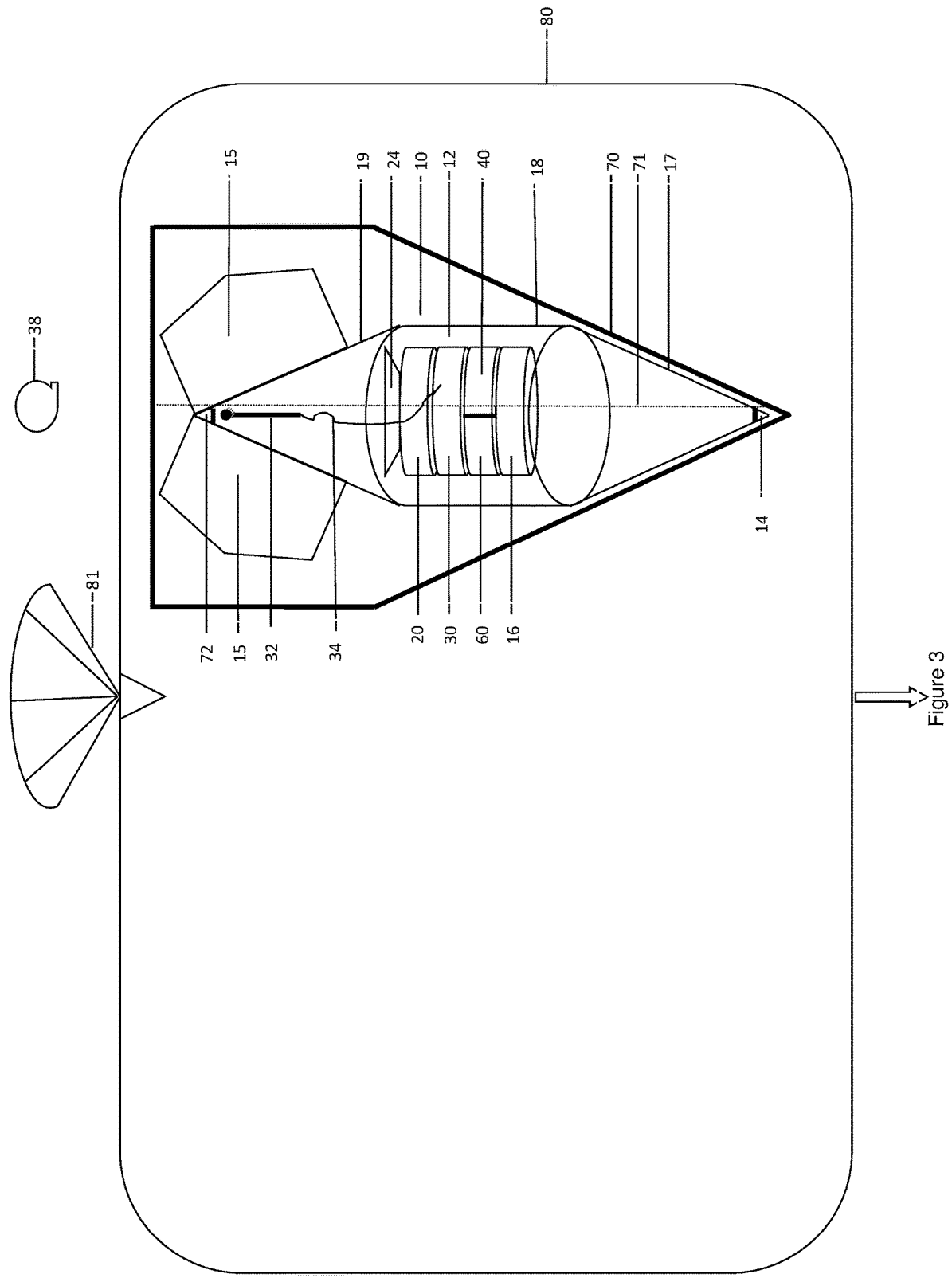
FIG. 3 depicts a penetrator remaining with the quiver after release of one of the penetrators from the quiver, with motion toward the celestial body indicated by arrow(s).

FIG. 3 shows the quiver 80 after leftmost penetrator 10 being released. The rightmost penetrator 10 will leave the quiver 80 to strike a different location of the celestial body's surface (not shown). In some embodiments, a single penetrator 10 may be carried by the spacecraft 90 and/or quiver 80. In certain facets, spacecraft 90 and/or quiver 80 comprising a plurality of penetrator(s) 10 with at least one penetrator 10 having an outer aeroshell 70 will comprise fewer total penetrator(s) 10 than if no aeroshell 70 was present. In certain embodiments, a plurality of quiver(s) 80 and/or penetrator(s) 10 may be used per spacecraft 90.

Figure 4:
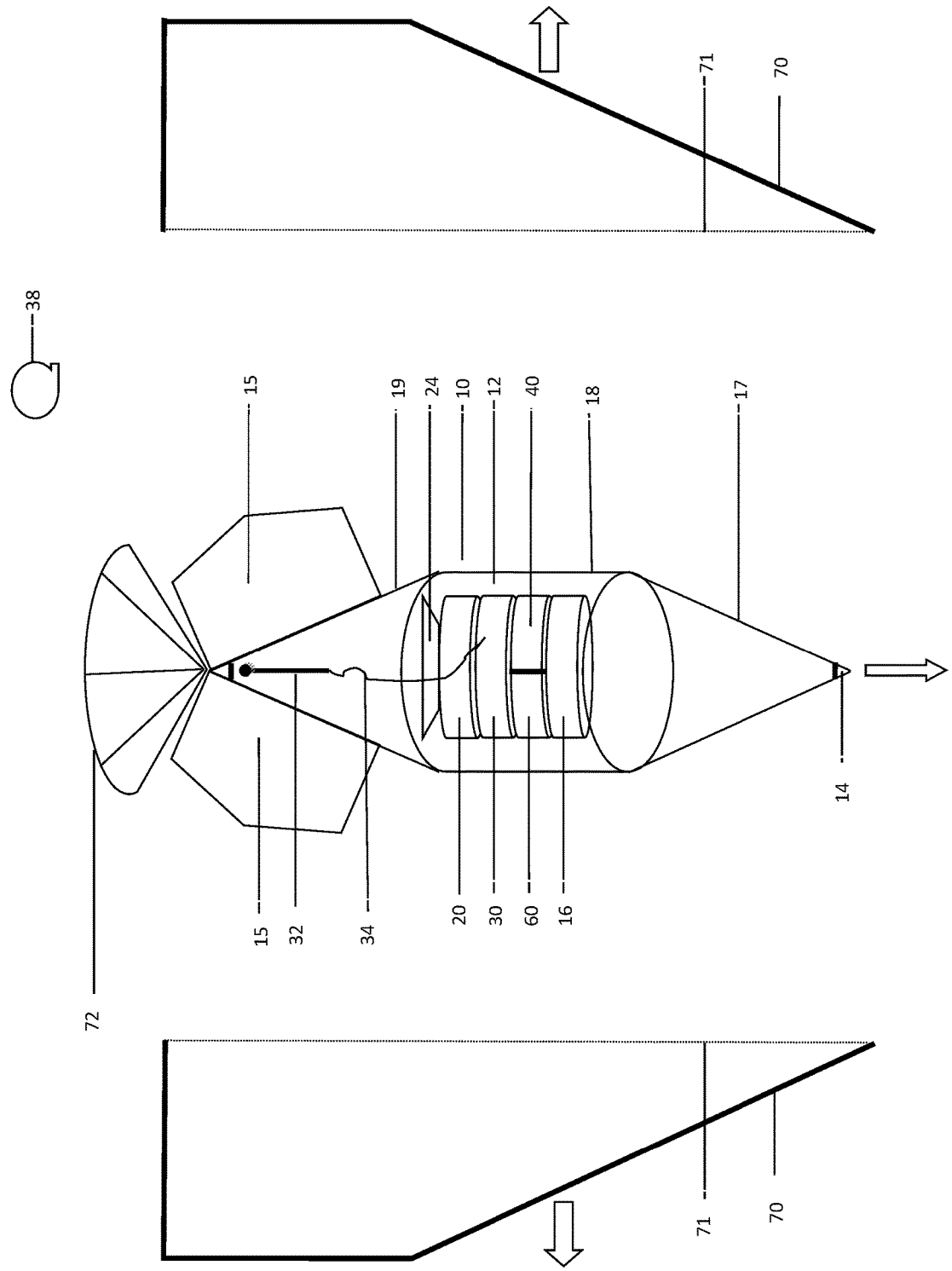
FIG. 4 depicts the released penetrator releasing an outer aeroshell in the celestial body's atmosphere, with motion of the aeroshell's pieces away from the penetrator and the motion of the penetrator toward the celestial body indicated by arrow(s).

FIG. 4 shows the penetrator 10 after the outer aeroshell 70 has separated into several pieces and has been released to move away from the penetrator 10. The penetrator 10 is shown with a descent speed control device 72, shown as a deployed parachute. A penetrator 10 that is primarily or completely gravity driven to impact with a celestial body's surface after release from the quiver 80 and/or outer aeroshell 70 is referred to herein as a "ballistic penetrator," while a penetrator 10 that is primarily driven by non-gravity acceleration is referred to herein as a "shot penetrator." In some embodiments, a shot penetrator propelled toward or into the surface by descent speed control device 72 such an attached rocket and/or jet engine (not shown) at or after time may be referred to as a "missile penetrator" to distinguish from embodiments wherein such an engine is not used.

Figure 5:
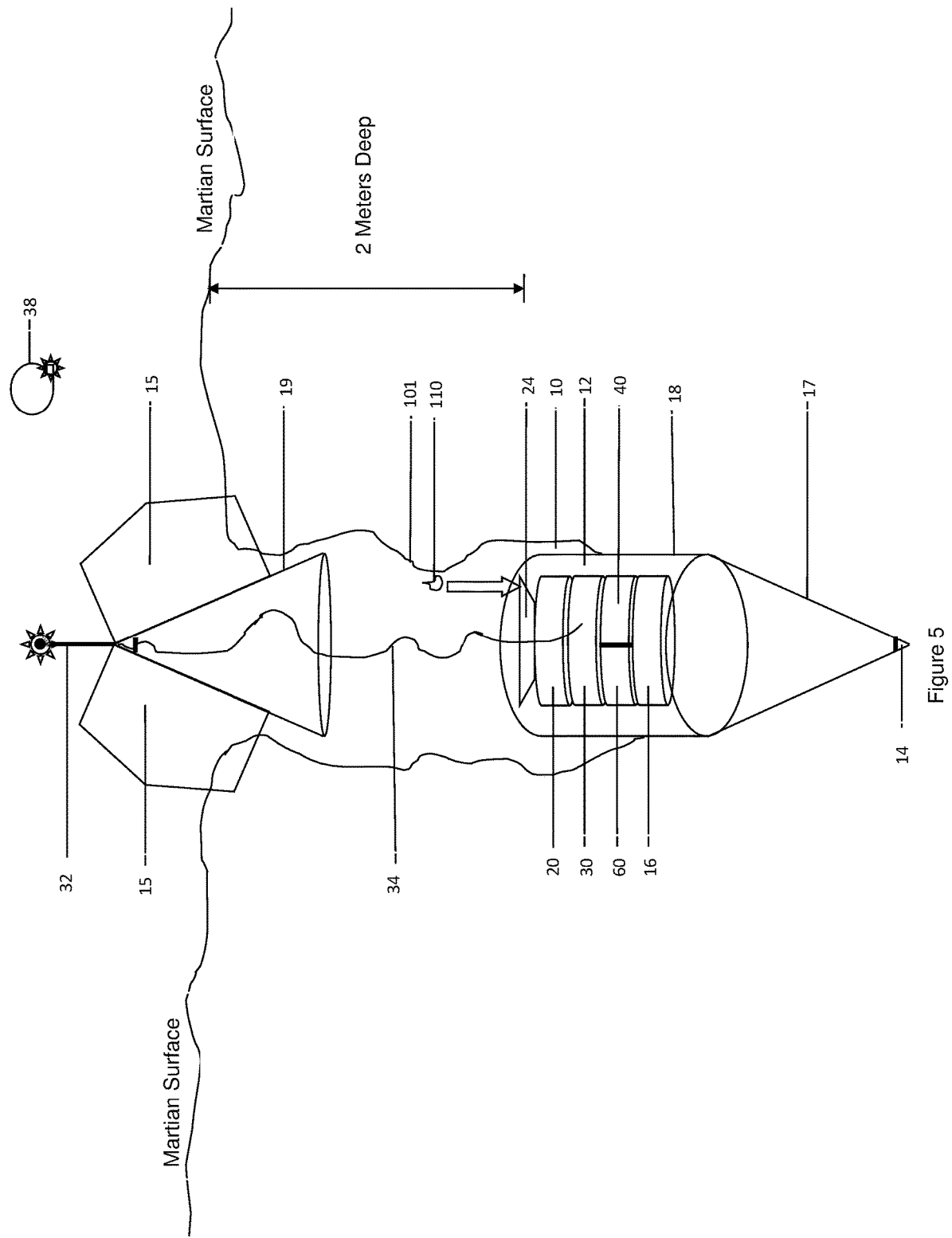
FIG. 5 depicts a penetrator, after impacting the celestial body at a perpendicular angle to the celestial body's surface, conducting life detection experiment(s) and communicating the results to a separate communication relay network.
Figure 6:
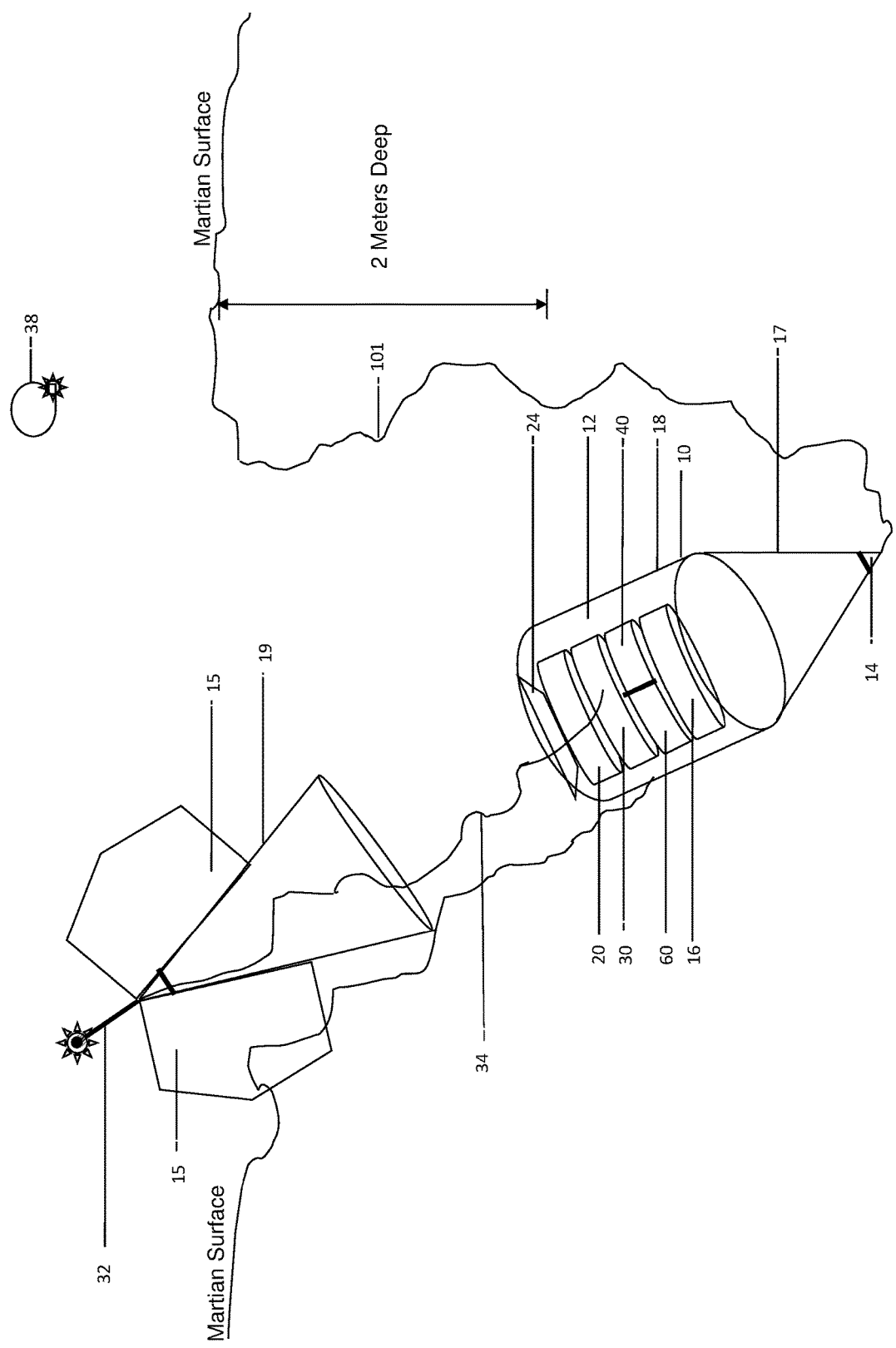
FIG. 6 depicts a penetrator, after impacting the celestial body at a non-perpendicular angle to the celestial body's surface, conducting life detection experiment(s) and communicating the results to a separate communication relay network.

FIGS. 5 and 6 shows the penetrator 10 at rest after impact with the celestial body's surface, depicted as a Martian surface. Though the penetrator may be designed to remain as one piece after impact, in many embodiments, the different body sections comprises separable body sections and/or the different parts of the equipment payload 12 (e.g., the penetrator 10 splits into two or more pieces). In some aspects, different sections of the penetrator 10 are connected by one or more umbilical wire(s) 34. For example, as shown, the scientific equipment package 20 and part of the communication device 30 may be contained in the mid-body section 18, while the antenna 32 being operatively associated with an aft-body section 19 that separates before, during and/or after the time of impact with a surface, with an umbilical wire 34 connecting the antenna 32 and/or aft-body section 19 to mid-body section 18, thus operatively connecting different parts of the partly separated equipment payload 12. As shown, in some facets, the aft-body section 19 comprises a depth achievement device 14 such as aerodynamic fins 15 that also impedes penetration of all or part of the penetrator 10 (e.g., a separable aft-body section 19) into the celestial body's surface, so that a limited depth is achieved for the aft-body section 19 and associated antenna 32. In contrast, the depth achievement device 14, which generally comprises a hardened surface, aids penetration of the front body section 17, mid-body section 18 and associated celestial body sampling device, which is now exposed to the Martian environment by separation of the mid-body section 18 and aft-body section 19. Loose celestial body's surface material 110 from the walls of the hole 101 created by the penetrator's 10 impact falls into the celestial body sampling device 24, shown as a funneling pan that passively collects and channels the material into the celestial body's surface material 110 into the scientific equipment package 20 that conducts a life detection experiment. The results of the life detection experiment are transmitted via the communication device 30 and the umbilical wire to the deployed antenna 32, which radiates an electromagnetic signal (shown as a star at the top of the antenna) to communicate the results to the separate communication relay network 38 that detects the radiated electromagnetic signal (also show as a star).

In specific aspects, the communication network 38 may comprise a ground based relay (e.g., a lander, another penetrator 10) (not shown), an atmosphere borne relay (e.g., a balloon, a drone, a sub-orbital craft) (not shown), a space based relay (e.g., a satellite, an orbiting spacecraft) (shown), an Earth based satellite dish (not shown), or a combination thereof. In some aspects, the communication network 38 may be a plurality of communication network(s) 38. In specific aspects, the communication network 38 conveys ("relays") the information for analysis at a laboratory (e.g., an Earth based laboratory, and Earth based investigator) and/or instructions to the penetrator probe 10 and/or quiver 80.

In other embodiments, an area that may be targeted for a penetrator 10 may include an area not easily accessible by a conventional rover or lander, such as for example, a lava tube, a cave, a karst, a crater gully, steeply inclined area, a liquid plume, a gas plume, or a combination thereof. In other embodiments, a consolidated mudstone (e.g., Yellowknife Bay at the Gale Crater of Mars) is targeted by the penetrator 10 as it is contemplated that organic material (e.g., past or present life) may be preserved from environmental damage (e.g., radiation, oxidation) in such locations.

In further embodiments, a plurality of penetrators 10, either same or different type (e.g., different shape(s), different equipment payload(s) 12, different optional component(s), etc.), are used to deliver one or more equipment payload(s) 12 to various locations on the celestial body(s) surface and/or different depths upon impact with the surface. A plurality of penetrators 10 (e.g., about 2 to about 10,000; about 2 to about 6, about 5 or 6) could be randomly scattered or non-randomly targeted to selected areas (e.g., covering meters, kilometers, etc.) of the celestial body's surface. In some aspects, a plurality of penetrators 10 may be used at the same location ("site") and/or a plurality of locations (e.g., across the same type of terrain, across different types of terrain) to promote obtaining and transmitting data collected by the equipment payload 12 (e.g., a scientific equipment package 20) via the communication device 30. It is contemplated that use of a plurality of penetrators 10 and target locations will increase the likelihood of survival and success of at least one penetrator 10 during use (e.g., high speed impacts), increase the amount of data from life detection experiment(s) and optionally other scientific data of interest, and/or expand data sampling for improved scientific evaluation and reliability by statistical analysis of data from a plurality of penetrator probes 10. In other embodiments, a plurality of penetrators 10 may be used in the analysis of a plurality of celestial bodies (e.g., such as in order to survey a star system, a planet-moon system, etc., for life).

SPECIFIC EXAMPLES

The general effectiveness of various embodiments are demonstrated in the following Examples that illustrates some methods for preparing compositions. The following Examples are provided so that the embodiments might be more fully understood, and is illustrative only and should not be construed as limiting in any way. Starting materials are made according to procedures known in the art or as illustrated herein.

Example 1: Penetrator Description

The penetrator system may be used for delivering a scientific equipment package to the subsurface of a celestial body, using Mars as an example. The penetrator delivery system may be based on penetrator designs used for military applications. The penetrator delivery system may piggyback on another mission's spacecraft.

This embodiment uses the mass balance opportunity of the Mars Balance Mass ("EBMD") deployment sequence. The penetrator is contemplated to be fit into the EBMD available volume. The penetrator "nose" may be machined from tungsten, so this is the same mass as the material it is displacing from the ballast mass. A small payload (cylindrical) volume may be made of steel and will house electronic(s) and battery(s). It is contemplated in some embodiments that this mass does not reduce the total ballast mass by more than about 10%. The penetrator system generally will be deployed (e.g., released) high in the Martian atmosphere when the other mission's spacecraft reaches Mars. The penetrator(s) in this example may be passive (no propulsion) and designed to fall ballistically to impact the surface.

The communications may be accomplished via an omni antenna which deploys upon impact and trails an umbilical cable down the tunnel to the penetrator and scientific equipment package, and may incorporate a similar approach used in the Deep Space Probe 2 probe. In some aspects, the scientific equipment package(s) may include a piece of equipment capable of conducting at least one experiment selected from life detection, seismometry, thermal measurement, and geodesy.

In another alternate design configuration of the balance mass, the deployment scheme for this approach separates the discarded balance mass after ejection from an aeroshell. The design of this alternative penetrator includes a passive sample of surface material collection technique using a cavity at the rear of the device as a sampling device that catches material falling after the penetrator reaches the deepest extent of its travel into the surface material.

It is contemplated that the relative merits of both design concepts, energy storage concepts such as miniature fuel cells, in addition to primary batteries which are the baseline approach, will be evaluated for selection for use in various embodiments, particularly in conjunction with the required power and duration to accomplish mission objectives for various equipment payload(s).

It is contemplated that a benefit of the penetrator system will be providing devices and methods to access the sub-surface environment on Mars and/or a networked approach, since multiple probes can be carried and deployed on each mission. It is contemplated that the balance mass sequenced ejection will provide a good degree of separation between the impact sites of the individual penetrator(s), which should improve the robustness of the probes, since the failure of an individual probe does not result in a total loss of science data. It is contemplated that many types of Mars science can benefit from the penetrator system, as due to relative simplicity of design to other types of spacecraft, relative low cost, and/or the ease to integrate into the existing Mars ballast mass configurations.

It is contemplated that a penetrator's impact depth achievement and function prior to and after impact may be tested by elevation and release above a celestial body (e.g., Earth), including very high altitude drops, using apparatus other than a spacecraft, such as, for example, via tower drop(s), balloon drop(s), airplane drop(s), sub-orbital rocket propulsion and return to surface, or a combination thereof.

Example 2: Computer Modeling of Penetrator Impacting an Extraterrestrial Surface at a 90 Degree Angle Hydrocode computer modeling was used to determine the deceleration profile, depth achieved, and impact tunnel contours on clay type soil using a Deep Space Probe 2 penetrator design testing results for calibration. Calibration parameters were a normal-to-the-surface 90° incidence using shot #9, an impact speed of 172 m/s, and a clay surface material. These calibration parameters produced a forward-body section penetration of 0.38 meters and an aft-body section penetration of 0.2 meters.

The grid was generated to model the penetrator's effect on the impacted material evaluated the initial impact velocity, penetrator parameters (e.g., mass, shape), and the angle of entry to determine penetration depth. The model was run using soil that matched the clay type soil and the Deep Space Probe 2 penetrator design, with the grid mesh adjusted to achieve the model's results. In the model, the penetrator produced a relatively small spray of ejecta when burrowing below 10 cm. After about 0.9 milliseconds the penetrator passed through 10 cm depth while producing an ejecta pattern resembling a common cratering process with a small cone of material forming on the surface. The aft-body would be interacting with the region of cone material. After another millisecond, the 20 cm deep tunnel showed indications of wall tapering. At about 10 milliseconds the penetrator had stopped at about 39 cm deep. The model was consistent with Deep Space Probe 2 testing results.

Through the modelling simulation (Aerojet Rocketdyne, 2001 Aerojet Road, Rancho Cordova, Calif. 95742-6418) for the first penetrator configuration (the test results of the Deep Space Probe 2 project were duplicated and thereby calibrate the soil properties, mesh sizes, and other model parameters). The model then was used to project what depth could be achieved with the baseline penetrator design. A depth of approximately 1.2 meters was shown to be possible for the assumed parameters.

Example 3: Computer Modeling of a Penetrator and Impacting Extraterrestrial Surfaces Computer modeling (Aerojet Rocketdyne) developed for military applications has been used for calibration runs for a model penetrator. A Deep Space Probe 2 type penetrator impact of a clay-like soil composition representative of the target material previously used for the Deep Space Probe 2 testing. The previous Deep Space Probe 2 testing data were used to "anchor" computer model results. The computer model data showed good agreement with the testing data. Computer modeling for sensitivity analysis of various impact velocities was conducted and indicated that the penetrator is capable of reaching a depth of one meter or more below the Martian surface. Computer modeling has also been conducted varying penetrator design (e.g., round vs. pointed nose; penetrator diameter, etc.), impact velocity, soil composition, and/or impact angles/angles of impact incidence.

Example 4: Computer Modeling of a Penetrator

It is contemplated that computer model simulations of impact penetration using variations in, for example, soil composition, angle of impact incidence, etc. will aid in modifying or improving penetrator design; provide data on deceleration profiles, impact generated tunnel contours that may aid in modifying or improving scientific equipment package selection and design; or a combination thereof. It is contemplated that a test range such as the Mojave Desert test range (New Mexico; California) may be used to simulate Mars-like surface material (e.g., soil, rock) for penetrator (e.g., ground penetrating demonstration of: a delivery system (e.g., an aircraft), depth (e.g., average depth) of penetration evaluation, scientific equipment package/life detection and/or communication device parameters in the penetrator(s) (e.g., impact survivability), etc.

Example 5: Computer Modeling of Penetrator Impacting an Extraterrestrial Surface at a Degree Angle The computer model of Example 1 was modified to determine the sensitivity to a less than nominal entrance angle (i.e., 70 degrees relative to the surface). Final penetration depth was reduced to 25 cm, and the penetrator's 10 horizontal motion widened the tunnel due to sideways movement ("sliding") in the soil.

Example 6: Alternative Penetrator Scientific Equipment Package Experiments: Detection of a Mineral or Life Supporting Sub-Surface Reservoir In some embodiments, a penetrator may be used in scientific analysis (e.g., analysis of terrestrial materials) and applications, and comprise one or more pieces of scientific equipment for various measurements and detection activity (s).

For example, a penetrator may comprise a piece of scientific equipment for measuring microbial gradients (or depletion thereof). Such measurements by way of example of microbial gradients surrounding heavy metal concentrations at and below the surface may used to detect an ore comprising metal that may be mined; measuring microbial gradients associated with pollution digesting microbes may be used for pollution detection/control applications; and measuring microbial gradients associated with soil may be used for nutrient detection for agricultural applications.

In some embodiments, the microbial detection equipment may detect microorganisms specifically associated with a particular type of ore, reservoir (e.g., water), or other feature of terrestrial body, and thus be used to prospect for useful minerals and/or resources. For example, a plurality of penetrators impacting an area may be used to survey an area for such ore associated microbes, with detection of sub-region(s) within the area that have the presence and/or higher concentration of ore associated microorganism(s) being indicative of a nearby ore body relative to penetrators that don't detect or detect a lower concentration of ore associated microorganism(s). In specific aspects, one or more penetrator(s) may comprise a piece of scientific equipment that can detect ore, reservoir(s), and/or other resources using scientific measurements other than biological material detection (e.g., life detection, specific microorganism detection), and may combine such scientific measurements with biological material detection to identify site(s) of a desired resource deposit(s).

Magnetic field changes in a celestial body typically due to a metallic/magnetic ore. A piece of scientific equipment such as a magnetometer may be used to measure changes in magnetic field property(s) using proton-precession, Overhauser effect, fluxgate, optical absorption, etc. and detect ore including iron sulfide mineral such as greigite, pyrrhotite; iron and/or iron titanium mineral such as magnetite, titanomagnetite, titanomaghemite, titanohematite, ilmenite, banded iron formation; burning coal (e.g., pyrite that becomes convert to magnetite during combustion) while the penetrator is in descent or after impact; or a combination thereof.

Electromagnetic detection may be used to measure changes in material's electrical conductivity and/or resistivity. Electromagnetic detection typically uses a piece of scientific equipment such as an electromagnetic transmitter to create an alternating electromagnetic field to induce electrical currents and then measures the induced magnetic field in ore to determine ore electromagnetic properties, and detect ore such as sulphides having lead or copper, some manganese minerals, graphite, magnetite, pyrite, or a combination thereof.

A piece of scientific equipment for electrical activity detection, such as for electromagnetic conductivity measurements, self-potential measurements, electrical resistivity measurements, direct current resistivity measurements, induced polarization measurements for interface ionic polarization and/or mise-a-la-masse measurements for resistivity, may be used to detect a mineral deposit (e.g., a sulfide mineral) and/or hydrological structures (e.g., water saturated rocks, clay, zeolite, metallic luster mineral(s)). For example, electrical currents in surface material whether natural or created by an electrical device is typically used to detect groundwater table and the location of bedrock. Direct current resistivity measurements may be used that has particular use in identifying a void (e.g., a cave) that may be empty, contain gas, and/or fluid (e.g., water). Induced polarization uses ground based electrodes connected to a receiver to measure the resistivity and chargeability of surface material and may detect conductive ore such as those identified by electromagnetic detection techniques.

Gravimetry measurements of variations in a gravity field by a piece of scientific equipment such as a gravimeter may be used to detect density contrasts such as to identify low density ore (e.g., fossilized bacteria, weathered kimberlite, halite, etc.), a high density ore (e.g., hematite, chromite, barite), and/or detect a geological structures such as an anticline, a salt dome, a fault, an oil deposit, an ore containing lead, zinc, iron, pyrite, or a combination thereof.

Seismic measurements by a piece of scientific equipment such as a seismometer and/or seismograph may detect seismic wave and/or sound velocity differences through material, reflection and/or refraction measurements. Such seismic measurements may be used to detect separate geological layers such as surface material, bedrock, as well as ore such as oil containing strata, gold, sand, tin, gravel, a mineral deposit, etc. In some embodiments, the impact of one or more penetrator(s) and/or a sound generating device (e.g., an explosive charge, a mechanical percussion generating device, a mechanical vibration generating device) that may be part of the penetrator's equipment package may be used to create seismic and/or sound waves that for measurement and detection of surface material features (e.g., ore deposits).

Piezoelectric measurements may be conducted by a piece of scientific equipment such as a piezoelectric sensor to detect an ore (e.g., quartz).

Detection of the chemical(s) in a sample of surface material, by a piece of scientific equipment for chemical detection such as one that conducts atomic emission spectroscopy (e.g., inductively coupled plasma atomic emission spectroscopy, spark/arc atomic emission spectroscopy), may be used to detect metal ion(s), element(s), etc., as well as chemical alterations in surface material (e.g., rock) by metasomatism (i.e., hydrothermal water circulation, other fluid circulation). In some embodiments, a gas may be measured, including during or after impact of a penetrator, such as for use in detecting an ore such as mercury.

Radiological measurements by a piece of scientific equipment such as a gamma-ray spectrometer, a Geiger counter, a scintillometer, etc. can detect ore containing a radioactive element/isotope such as ore comprising thorium, uranium, potassium, radium, etc.

A piece of scientific equipment for remote sensing of various types of electromagnetic radiation (e.g., visible light, ultra-violet light, infrared light) may be used while the penetrator above the atmosphere during decent, and may detect ore (e.g., silica, an iron hydroxide mineral, clay).

Optical light emission/absorption measurements by a piece of scientific equipment such as an optical spectrometer (e.g., a spectrophotometer, a spectroscope, a spectrograph) may be used to detect various types of ore based on spectral absorption.

X-ray emission/absorption measurements by a piece of scientific equipment such as an X-ray fluorescence spectrometer may be used to detect various ore types via X-ray spectroscopy, wavelength dispersive spectroscopy, X-ray diffraction, etc.

Ultraviolet emission/absorption measurements using a piece of scientific equipment such as a laser may detect a fluorescent ore (e.g., hydrozincite, scheelite, a tungsten containing mineral).

Radio wave emission/absorption measurements by a piece of scientific equipment, such as used in ground-penetrating radar, may detect an ore (e.g., electrically resistive rock) and/or a void (e.g., a cave) that may be empty, contain gas, or fluid (e.g., water)

A piece of scientific equipment for measuring thermal/infrared energy may be used to detect hydrological and/or hydrothermal systems.

In some aspects, a sterile celestial body and/or location may be used as a negative control for a life detection experiment, while a location previously identified has having life may be used as a positive control. For example, in certain embodiments, a penetrator system may use Earth as a positive control for comparison of results obtained by a penetrator system used in extraterrestrial celestial body(s) (e.g., Mars, Titan, Europa, Ganymede, larger asteroids, comets, etc.). In another example, a celestial body that is known to be devoid of life (e.g., the Moon of Earth) may be used as a negative control.

Example 7: Subsurface Location of Biological Materials

It is contemplated that biological material such as living or preserved non-living microbial life may exist at, near, and/or below the surface of an extraterrestrial body. It is contemplated that the surface material at the atmosphere (if present) or space interface (known herein as the "surface material interface") is drier and/or colder than material that is deeper (e.g., one or more meters deeper than the surface-atmosphere interface). It is also contemplated that shielding from cosmic, ultraviolet or other radiation and other environment conditions (e.g., thin atmosphere, wind, cold-freezing temperature, etc.) that may damage or kill the biological material increases with depth from the surface material interface. It is contemplated that a plurality of penetrators that conduct life detection experiment(s) at different location(s) and/or depth(s) would enhance the likelihood of detecting life on Mars where life is not uniformly distributed through all locations and/or depths.

For example, it is contemplated that non-frozen water (e.g., moisture, liquid water, aquifers, etc.) beneath the surface material interface may provide an environment more hospitable for life and/or organic molecules relative the surface material interface or a frozen subsurface (e.g., a subsurface permafrost/ice layer). Although microbes have been found within ice that are metabolizing, it is also contemplated that life may exist to be detectable at a subsurface or deeper layer due to periodic melting of ice to water in specific locations ("patches") in such material.

It is contemplated that in some embodiments, the deeper below the surface material interface, the greater the probability to detect life and/or biological molecules for at least several meters (e.g., up to about 10 meters). In one non-limiting example, it is contemplated that microbial life may be more readily detected from sample(s) of surface material obtained at about 1 meter or more below the surface material interface of Mars. However, a sample of surface material that may comprise biological material may be from the surface material interface and/or from underneath (i.e., below, beneath) the surface material interface.

Example 8: Sterilization of the Penetrator and Inclusion of a Self-Sterilizing Coating In specific aspects, the penetrator system (e.g., penetrator, quiver, etc.) is sterilized to kill life such as cell(s) and virus(s) (e.g., a bacteriophage) and destroy detectable terrestrial biomolecule(s) such as proteins, peptides, nucleic acids, carbohydrates, lipids, etc. In specific facets, the surfaces of the penetrator system are preferentially coated with a self-sterilizing coating comprising a coating material and one or more peptide(s), enzyme(s), or other biomolecules that kill and/or sequester (e.g., antigen-antibody binding) terrestrial life and/or biologically degrade contaminating terrestrial biological material(s). Sterilizing the penetrator system and/or coating the penetrator with a self-sterilizing coating will reduce or prevent false positive results when a scientific equipment package is used to detect one or more extraterrestrial biological material(s), help prevent the contamination of an extraterrestrial body with cell(s) and/or virus(s) from Earth and/or to meet any regulatory body's concern regarding such contamination (e.g., planetary protection). For example, selection of the biomolecules for the self-sterilizing coating may be coordinated with the type of experiment(s) of the scientific equipment package, such as: inclusion of nuclease(s) in a coating to reduce or eliminate contaminating terrestrial nucleic acids when a life detection experiment will assay for the presence of extraterrestrial nucleic acids; inclusion of anti-microbial peptide(s) and/or enzyme(s) to reduce or eliminate terrestrial microorganism(s) when a life detection experiment will assay for the metabolic activity of an extraterrestrial organism, etc., as such potential contamination has been used to critique other life detection probes (e.g., the "Viking lander" problem). Examples of coatings that comprise enzyme(s), peptide(s), or other biomolecules that may be used to kill terrestrial life and/or degrade contaminating terrestrial biological material(s) are described in U.S. Pat. Nos. 8,497,248, 7,932,230, 7,939,500, 8,618,066, and 8,388,904, and U.S. patent application Ser. Nos. 10/655,345, 10/884,355, 11/865,514, 12/243,755, 12/696,651, 12/882,563, 13/085,061, 14/097,128, 14/093,347, 14/151,455, 14/156,007, and 14/795,608, each incorporated herein by reference.

Example 9: Life Detection Experimental vs. Sterilized Control Samples

Due to biological processes such as enzyme activity, life in a sample of surface material will be strongly indicated by rapid and/or greater total amount release of a chemical product of a molecule (e.g., a biomolecule) utilized by living cells during normal metabolic processes, relative to the rate and/or amount of product created ("product production") of the chemical product by an abiotic ("non-life") reaction in a like control sample (e.g., a negative control sample) of surface material with little or no living cells present after undergoing contact with one or more sterilizing agent(s). As used herein, a sterilizing agent refers to a substance (e.g., an anti-metabolite chemical) and/or process (e.g., heating, irradiation, and in some cases shading from light/radiation) that kills and/or greatly (more than 50%) retards the metabolism of a living cell and/or biomolecule(s) (e.g., enzyme) activity(s) and generally does not greatly alter the product production of a non-life based chemical reaction. An example of a non-life based chemical reaction would be a chemical reaction catalyzed by an inorganic mineral found in surface material, e.g., $CO_2$, methane, H2O.

For example, living cells found on Earth are adapted to live within specific environmental conditions and are often sensitive to inactivation (i.e., dying) by changes in environmental conditions relative to an inorganic chemical reaction. Only a relatively few organisms found on Earth are adapted to survive heating at or near that of boiling water (i.e., 100° C. on Earth) for several minutes, and a reduction in a chemical reaction's product production that is achieved by heating a sample of surface material to such a temperature would be indicative of sterilization of living cell(s) and thus the presence of life, given that inorganic chemical reaction are far less susceptible and often generally impervious to inactivation by such temperatures shifts.

Achieving a comparative reduction in product (e.g., metabolite) production between test and sterilized samples of surface material, particularly modest amount(s) of a sterilizing agent would be used, would be strongly indicative of life. For example, different amounts of the sterilizing agent may be used, such as heating at different temperatures to determine a temperature at which product production is reduced. In a cold extraterrestrial environment, such as typically found on Mars (e.g., a measured surface temperature maximum of about 27° C.), it is contemplated that Martian life may be adapted for relatively low temperatures (e.g., a hyperpsychrophile, a psychrophile, a mesophile) and thus potentially more susceptible to sterilization by heating (e.g., contact with less than about 100° C.) than most terrestrial organisms.

Additionally, administration of the sterilizing agent during an ongoing reaction producing a product that interrupts (e.g., inhibits) reaction would be strongly indicative of the presence of life. It is contemplated that as greater amounts of radiation (e.g., UV, cosmic, solar wind, etc.) affect the surface of Mars, a Martian organism may be adapted to be more resistant to a type of radiation (e.g., UV) and/or adapted to live in a radiation resistant ecological niche (e.g., in the shade, under the surface-atmosphere interface, etc.). It is further contemplated that such a Martian life form may be adapted to change metabolic activity (e.g., increase, decrease) when placed in a shaded or dark environment relative to a comparison sample that is maintained in a non-shaded or illuminated environment.

Example 10: Life Detection of Extremophiles

It is contemplated that in certain aspects, extraterrestrial life may possess similarities to organisms adapted for various environments (e.g., extremophiles) found on Earth, and the scientific equipment package may include one or more life detection experiment(s) for a hyperpsychrophile, a psychrophile, a mesophile, a thermophile, a hyperthermophile, an extreme acidophile, an acidophile, an alkaliphile, an extreme alkaliphile, an extreme halophile, a methanogen, etc. Samples may be subjected to extremes of temperature, salt, pH and/or other conditions during life detection experiment(s) to compare and contrast results in order to obtain evidence of life that may have environmental tolerance(s) suited for, and preferentially metabolically active in, extremophile condition(s). Further, it is contemplated that extremophile(s) may be susceptible to being over-fed by any nutrient(s) provided during a life detection experiment, so that difference(s) in product production between a test sample and a sterilized control sample may be transitory, with only a limited amount of time (e.g., minutes, hours, days) before over-fed extremophiles become metabolically inactive (e.g., quiescent, dead).

Example 11: Life Detection Experiments Conducted by a Scientific Equipment Package In general embodiments, the scientific equipment package will contain a piece of scientific equipment, such as that suitable for detection of a biological material (e.g., life-detection equipment) from a sample of surface material. In some aspects, such a sample of surface material that undergoes a scientific experiment may be a fraction of surface material obtained from a celestial body (e.g., eluate from a soil sample moistened with an assay solution such as nutrient broth, a polymerase chain reaction solution, etc.).

In specific facets, to conduct one or more life detection experiment(s), the scientific equipment package will comprise one or more piece(s) of scientific equipment capable of: a metabolic experiment (e.g., a radiolabeling metabolic study)/test to distinguish metabolic chemistry (e.g., a chiral left-right "CLR" experiment) of a living cell (e.g., a microorganism "microbe"; a cell of an organism) from a non-living chemical reaction; one or more studies done by or similar to another spacecraft (e.g., the Viking 1 and 2 lander spacecraft, the Curiosity rover, etc.); an experiment capable of detecting biochemical differences relative to terrestrial life that would be indicative of the emergence of life independently from the events on Earth (i.e., a different abiogenesis event than that for life existing on Earth) and/or that the extraterrestrial life and terrestrial life have the same or similar biochemistry; an experiment to detect active life (e.g., metabolically active vs. quiescent life); a chemical sampling test to find signs of life; a nucleic acid detection experiment such as one using, for example, a DNA sampler, a polymerase chain reaction device, or a device for "faxing" sequences; a sound detector; a fluorescence detector and/or a light detector; an energy emitter (e.g., a heat source, a light source, an ice melting device); or a combination thereof, as would be known to those or ordinary skill in the art (see, for example, Skelley et al., Journal of Geophysical Research, 112 (G04S11): 1-10, 2007).

Example 12: A Radiolabeled Metabolic Study Life Detection Experiments Conducted by a Scientific Equipment Package A life detection experiment conducted by a piece of scientific equipment may comprises a radiolabeling metabolic study, wherein a metabolizable molecule that comprises a detectable radioisotope (e.g., a nutrient broth comprising a radiolabeled biomolecule) is contacted with the sample. Changes in the radiolabel's presence in the molecule or presence a chemical reaction product, such as detection of the loss of radiolabel from the sample material and/or gain of the radiolabel in an area away from the sample material, are typically measured. For example, often the rate and/or amount of release (e.g., appearance and/or accumulation) of radiolabeled product (e.g., a radiolabeled gas such as $CO_2$) would be indicative of the conversion of radiolabeled biomolecules (such as a radiolabeled sugar, amino acid, etc.) by a living cell via metabolic activity, particularly in comparison to reduced product production by a sterilized control sample. In some embodiments, another molecule (e.g., a non-chiral molecule that is not radiolabeled, a metabolizable molecule, a nutrient) is contacted with the sample of surface material upon simultaneous or subsequent contact of a radiolabeled molecule to potentially stimulate metabolic activity to enhance detectable changes in the radiolabel's presence.

Example 13: A Radiolabeled Chiral Biomolecule Life Detection Experiments Conducted by a Scientific Equipment Package A stereoisomer molecule has the same sequence of bonded chemical groups/atoms ("moieties"), though the three dimensional positions of the moieties are different between enantiomers of the molecule. An enantiomer is one of two non-superimposable versions of the stereoisomer. The two enantiomers ("optical isomers") of a stereoisomer are mirror images of each other based on the three dimensional positions of the moieties.

In the art of biochemistry, chirality in a molecule usually refers to a stereoisomer molecule having a non-superimposable mirror image. An atom (e.g., a carbon atom) capable of forming multiple chemical bonds to different moieties is often the feature that causes chirality. An example of chirality in an object are human hands, with the sequence of attached fingers analogous to the sequence of moieties attached to a carbon atom in an amino acid. A chiral molecule (e.g., a chiral biomolecule) may be levorotatory ("left-handed," "L") or dextrorotatory ("right-handed," or "D"), and an enantiomer may be designated "D-" or "right-handed" vs. "L-" or "left-handed".

On Earth, living cells predominantly utilize only one enantiomer or the other of various molecular stereoisomers to conserve energy during metabolic activity (e.g., anabolism, catabolism). For example, amino acids and larger biomolecules such as peptides and proteins comprising amino acids used by terrestrial cells preferentially utilize L-amino acids with only the occasional presence of D-amino acids in such biomolecules. Terrestrial organisms also strongly prefer D-carbohydrates (e.g., D-glucose) over L-carbohydrates. Enzymes of terrestrial organisms preferentially act on molecules of one chirality, such as enzyme that selectively accelerates hydrolysis of proteins comprising L-amino acids.

It is contemplated that an extraterrestrial life will likely use water and carbon based chemistries analogous to the biochemistry of Earth-based life. Though it is contemplated that an extraterrestrial life may have the same preferences of molecule chirality as found in terrestrial life, it is also contemplated that such extraterrestrial life may predominantly utilized one or more different enantiomers of chiral molecule(s), such as largely utilizing, for example, D-amino acid(s) and/or L-carbohydrate(s). It is also contemplated that an extraterrestrial life may use both types of chirality in some or all molecules utilized by the extraterrestrial life. It is contemplated that if extraterrestrial life preferentially uses the same chiralities as terrestrial life, then it may be related to, or have the same origin, as terrestrial life.

Though non-life chemical reactions tend to use both types of chirality, a greater product production by a sample of surface material over time relative to a sterilized control sample of surface material is indicative of life regardless of any preference, or lack thereof, for use of chiral molecule(s) in a chemical reaction. Life in a sample of surface material is strongly indicated by a greater product production preferentially of one enantiomer of a chiral molecule over the other enantiomer, relative to a like reaction using a sterilized control sample.

In some embodiments the same radioisotope(s) may be used for each pair of supplied enantiomers, or different radioisotope(s) may be used for one or more different pair(s) of enantiomers when a plurality of different chiral molecules are used. For example, a right-handed enantiomer may be labeled with one radioisotope (e.g., radioactive carbon), and the left-handed enantiomer may be labeled with another radioisotope (e.g., heavy water containing deuterium) and both enantiomers contacted to a sample of surface material comprising microbes. The microbes may preferentially metabolize the only one or the other enantiomer, and predominantly produce a detectable chemical product containing one or the other radioisotope (e.g., an emitted gas such as carbon dioxide containing radioactive carbon vs. release of an emitted gas containing deuterium). In contrast, a like sterilized sample of surface material containing and/or contacted with an environmental agent that may promote chemical reaction(s) that could generate reaction product will often indiscriminately produce a more equal mixture of both enantiomers comprising the two detectable radioisotopes.

Example 14: Selection of Carbon Based Molecules for a Metabolic Life Detection Experiment In specific embodiments, one or more radiolabeled chiral and/or non-chiral chemical(s) could be used. For example, rather than contacting a sample of surface material with a mixture of radiolabeled enantiomers (e.g., $^{14}$C-D-alanine and $^{14}$C-L-alanine; $^{14}$C-D-sodium lactate and $^{14}$C-L-sodium lactate) the sample of surface material would be contacted with one or the other enantiomer and compared to a like sterilized sample of surface material contacted with the same enantiomer. In other embodiments, one or more non-stereoisomeric radiolabeled molecules (e.g., $^{14}$C-calcium glycolate, $^{14}$C-glycine and $^{14}$C-sodium formate) may be selected for contact with the sample of surface material and a like sterilized control sample.

It is contemplated that a failure to show a difference in product production between the test and sterilized control samples for a particular molecule does not disprove the presence of extraterrestrial life, as that life may not metabolize the molecule. In some embodiments, providing various molecules allows for a greater possibility for supplying a molecule that extraterrestrial life can metabolize. For example, one molecule that may be converted into a detectable product may be supplied to a sample per each test in order to identify specific molecule(s) that undergoing reaction(s) in the sample(s) of surface material. Such identified reactive molecule(s) may be selected and/or non-reactive molecule(s) avoided in further experiment(s) (e.g., life detection experiments by subsequent penetrator(s))

In the case of supplying two (or more) enantiomers of a molecule, failure to preferentially produce a product of one enantiomer over the other does not disprove the presence of extraterrestrial life in the case wherein the life may relatively non-preferentially metabolize both enantiomers, and life may be still indicated when there is a difference between the product production between the experimental sample and the sterilized control. It is contemplated that demonstration of a differing chiral preference (e.g., equal use for L and D amino acids) for Martian sample(s) of surface material relative to terrestrial life (e.g., L amino acid preference) would indicate that life on Mars originated separately from life on Earth, as all cells on Earth demonstrate a genetic and biochemical family similarity.

Example 15: A Radiolabeled Chiral Biomolecule Life Detection Experiments Conducted by a "Viking-Like Lander"

It is contemplated that a life detection experiment for a penetrator may use all or part of the experimental design features (e.g., molecule(s), radioisotope(s), atmosphere(s), pressure(s), temperature(s), etc. of any life detection experiment as would be known to those of skill in the art. For example, in the Viking landers' experiments, a 0.5 mL sample of Martian soil was obtained from the first few (e.g., about 4) centimeters of topsoil. Duplicate soil samples were sterilized by heating ("baking") the soil sample to 160° C. for three hours, a temperature selected to sterilize or greatly retard metabolism while not destroying non-biological chemical reactants that possibly could produce a false positive result. A 0.15 mL aqueous solution comprising the following dissolved chiral and non-chiral molecules ("aqueous solution") were contacted with the Martian soil samples in a test chamber having Martian atmosphere pressurized to 85 mb with Helium at 7° to 10° C. in a dark environment:

TABLE 1

Viking Lander Life Experiment Molecules

| Molecule | Concentration ($\times 10^{-4}$M) | Specific Activity (Ci/Mole) |
|---|---|---|
| $^{14}$C-calcium glycolate | 2.5 | 16 |
| $^{14}$C-DL-alanine | 5.0 | 48 |

TABLE 1-continued

Viking Lander Life Experiment Molecules

| Molecule | Concentration (× $10^{-4}$M) | Specific Activity (Ci/Mole) |
|---|---|---|
| $^{14}$C-glycine | 2.5 | 16 |
| $^{14}$C-sodium formate | 2.5 | 8 |
| $^{14}$C-DL-sodium lactate | 5.0 | 48 |

The carbon-based molecules selected for the Viking lander experiments were among those though to be created by abiotic processes on Earth (i.e., "Miller-Uray" compounds) and Mars prior to formation of life, and have been commonly utilized (e.g., metabolized) by various terrestrial soil microbes in disparate environmental conditions. It was thought by investigators such as Gibert Levin that one or more of such molecules would similarly be utilized by cells living in Marian soil.

Chromatographic spreading of the aqueous solution made the soil samples wet or moist. The released gase(s) were detected in a detector chamber that was connected to the test chamber by a baffle. A beta radiation detector was used to measure released radiolabeled gas at 4 then 16 minute time points over eight days.

Radiolabeled gas was produced in the non-sterilized soil sample and negligible radiolabeled gas released in the sterilized soil sample, with a gas release slowing after about 3 days. A second injection of aqueous solution produced about 20% radiolabeled gas release in the non-sterilized sample, with more radiolabeled gas gradually released over 2 months.

As heating at lower temperatures may produce partial or no sterilization of living cell(s), additional soil samples were tested by heating at reduced temperatures (i.e., 51° C., 46° C.) for 3 hours prior to contact with th e aqueous solution, and some amounts of radiolabeled gas was released, though less than in the non-heated soil sample. Soil samples maintained under Martian atmospheric conditions at 7° C. to 10° C. in the dark for up to 10 days produced radiolabeled gas upon injection with the aqueous solution, though soil samples stored 3 or 5 months did not produce radiolabeled gas after 1 or 2 contacts with the aqueous solution. Soil samples protected from ultraviolet radiation by shadow from rock produced radiolabeled gas release. The results of the Viking lander data has attributed the release of radiolabeled gas to a strong, unidentified oxidant in the soil sample reacting with the aqueous solution of radiolabeled molecules, though inactivation of the putative chemical oxidant by storage in the dark for more than 3 months was unexplained.

Example 16: Scientific Equipment Package for Measuring Nucleic Acids

In some embodiments the scientific equipment package contains one or more nucleic acid (e.g., RNA, DNA) detection devices. It is contemplated that extraterrestrial life may contain polymeric nucleic acids, and the presence of such polymeric biomolecules would be indicative of life as they are produced almost exclusively by biological processes. Such a nucleic acid detection package may include any nucleic acid detection device known to those of skill in the art (see, for example, Cobo F., *Open Virol J.* 6:104-114, 2012; Wang D., et al., *PLoS Biol.* 1(2):E2, 2003; Hu Y., *Molecular Techniques for Blood and Blood Product Screening. Advanced Techniques in Diagnostic Microbiology*: Springer; 2013. Chang C. C., et al., *Sensors (Basel)*, 12(6): 8319-8337, 2012; Motamedi M., et al., *J Global Infect Dis.* 3(3):293, 2011; Wu F., Hong T., Della-Latta P., *Nonamplified Probe-Based Microbial Detection and Identification. Advanced Techniques in Diagnostic Microbiology*: Springer; 2013; Balachandra K., et al., *B Dep Med Sci.* 36(3):145-152, 2013; Johnson G., et al., *Methods Mol Biol.* 943:1-16, 2013; Loeffelholz M., and Dong J., *PCR and Its Variations. Advanced Techniques in Diagnostic Microbiology;* 2013; Nurtjahyani S.D., and Handajani R., *J Biol Agr Healthcare.* 3(6):101-105, 2013; Tang Y. W., and Stratton C. W., *Advanced Techniques in Diagnostic Microbiology*: Springer; 2012; Versalovic J., and Lupski J. R., *Trends Microbiol.* 10(10 Suppl):S15-S21, 2002; Pernagallo S., et al., *Sensors (Basel).* 12(6):8100-8111, 2012; Nuriya H., et al., *J Clin Microbiol.* 48(11):3843-3851, 2010; Sul J., et al., *Cancer Lett.* 238(2):210-223, 2006; Bekkaoui F., et al., *Biotechniques.* 20(2):240-248, 1996; Hosseini S. M. J., et al., *Hepat Mon.* 9(2):150-153, 2009; Suzuki Y., et al., *J Clin Microbiol.* 48(1):57-63, 2010; Wong D. K., et al., *Hepatology.* 40(3): 727-737, 2004; Germer J. J., et al., *J Clin Microbiol.* 44(2):318-323, 2006; Wang F., et al., *BMC Med Genomics.* 6 Suppl 1:S15, 2013; Wiedmann M., et al., *PCR Methods Appl.* 3(4):551-64, 1994; Tsongalis G. J., *Am J Clin Pathol.* 126(3):448-453, 2006; Kricka L. J., *Clin Chem.* 45(4):453-458, 1999; Wang Y. F. W., *Signal amplification techniques: bDNA, hybrid capture. Advanced Techniques in Diagnostic Microbiology*: Springer; 2006; Ariffin S. N. F. A., *J Res Med Sci.* 1(1), 2013; Baumeister M. A., et al., *PLoS One.* 7(3), 2012; Ross R. S., et al., *J Virol Methods.* 101(1-2):159-168, 2002; Cho O, et al., *Hepatol Int.* 7(1):111-118, 2013; Freeman W. M., et al., *Biotechniques.* 26(1):112-122, 1999; Chauhan H., et al., *Vet World.* 2(5):179-182; 2009; Elnifro E. M., et al., *Clin Microbiol Rev.* 13(4):559-570, 2000; Ito K., et al., *Intern Med.* 52(2):201-211, 2013; Nicodème P., and Steyaert J. M., editors. *Selecting optimal oligonucleotide primers for multiplex PCR. Ismb:* 1997; Shuber A. P., et al., *Genome Res.* 5(5):488-493, 1995; Mackay I. M., et al., *Nucleic Acids Res.* 30(6):1292-1305, 2002; Brechtbuehl K., et al., *J Virol Methods.* 93(1-2):105-113, 2001; Weinberger K. M., et al., *J Virol Methods.* 85(1-2):75-82, 2000; Notomi T., et al., *Nucleic Acids Res.* 28(12):E63, 2000; Mori Y., et al., *J Infect Chemother.* 15(2):62-69, 2009; Cai Z., et al., *J Clin Virol.* 52(4):288-294, 2011; Zhang L. Q., et al., *Arch Virol.* 157(12):2383-2388, 2012; Ehrenreich A. *Appl Microbiol Biotechnol.* 73(2):255-273, 2006; Heller M. J., *Annu Rev Biomed Eng.* 4:129-153, 2002; Lucchini S., et al., Microbiology. 2001; 147(Pt 6):1403-1414; Kostic T., Butaye P., Schrenzel J. *Detection of Highly Dangerous Pathogens: Microarray Methods for BSL 3 and BSL 4 Agents*: Wiley; 2009; Behzadi P., et al., *Infectioro.* 35(3):6-10, 2013; Xu R, et al., *Anal Biochem.* 362(1):69-75, 2007; and Tu Q, et al., *Appl Environ Microbiol.* 79(16):5085-5088, 2013.)

For example, a nucleic acid detection device may use a non-amplified nucleic acid probe, an amplified nucleic acid procedure, a field-effect-based device, or a combination thereof. Non-amplified nucleic acid probes may be in a solid phase, in an in situ hybridization, a liquid phase, or a combination thereof; and may use, for example, a radiolabeled probe, a fluorescence labeled probe (e.g., fluorescence in situ hybridization), a dye labeled probe, an enzyme labeled probe, or a combination thereof. For example, a non-amplified nucleic acid probe may comprise hapten digoxigenin that can bind an antibody labeled with a dye or enzyme that produces a detectable product of a chemical reaction. A nucleic acid probe typically may comprise a nucleic acid and/or a peptide nucleic acid. An amplified nucleic acid detection procedure may include microarray devices; loop-mediated isothermal amplification of DNA; a probe amplification procedure such as cycling probe technique, a ligase chain reaction, a branched DNA technique, a hybrid capture assay that uses an antibody and detection agent that typically is luminescent, and an invader assay; a polymerase chain reaction ("PCR") and variants thereof, including real-time PCR, reverse transcription PCR, nested PCR, and multiplex PCR; or combinations thereof.

Examples of such a nucleic acid detection device include a DNA/RNA biochip and associated reagents capable of conducting a polymerase chain reaction and detection polymerized nucleic acids and/or DNA/RNA chips capable of distinguishing common progenitor DNA/RNA. Samples of surface material undergoing a nucleic acid detection experiment would have results compared to a like experiment lacking a sample of surface material as a negative control. For example, in some embodiments, a nucleic acid detection device may comprise a field-effect-based device (e.g., a biosensor device), such as an ion sensitive field effect transistor, an electrolyte-insulator-semiconductor, a charge modulated field effect transistor, a metal-insulator-semiconductor capacitor, a metal-oxide-semiconductor field effect transistor, or a combination thereof. Such field-effect-based device(s) generally detect changes in electrical charge (e.g., ions) that occur during hybridization (e.g., mismatch detection) and/or nucleic acid reaction(s) (e.g., enzyme catalyzed changes in a nucleic acid) that allows nucleic acid detection and/or sequencing by the field-effect-based device(s). In one example, an electrolyte-insulator-semiconductor that conducts PCR was able to detect the presence or absence of a nucleic acid amplification product without the use of a labeled nucleic acid probe (Chih-Sheng, J. H. et al., *Lab on a Chip*, 7:347-354, 2007). It is contemplated that in certain preferred embodiments, such nucleic acid detection device(s) that comprise a field-effect-based device, including semiconductor or chip based device(s), device(s) capable of nucleic acid label-free DNA sequencing, device(s) capable of piezoelectric detection of nucleic acid(s), or a combination thereof, known to those of skill in the art, may be used with a penetrator (see, for example, Rothberg, J. M., et al., *Nature* 475:348-352, 2011; Souteyrand, E., et al., *J. Phys. Chem. B* 101:2980-2985, 1997; Uslu, F., et al., *Biosens. Bioelectron.* 19:1723-1731, 2004; Pouthas, F., et al., *Phys. Rev. E* 70:31906, 2004; Ingebrandt, S., et al., *Biosens. Bioelectron.* 22:2834-2840, 2007; Fritz, J., et al., *Proc. Natl. Acad. Sci. USA* 99:14142-14146, 2002; Estrela, P., et al., *Electrochim. Acta* 50:4995-5000, 2005; Gongalves, D., et al., *Biosens. Bioelectron.* 24:545-551, 2008; Sakata, T., et al., *Mat. Sci. Eng. C* 24:827-832, 2004; Sakata, T., et al., *Jpn. J. Appl. Phys.* 44:2854-2859, 2005; Kim, D., et al., *Jpn. J. Appl. Phys.* 42:4111-4115, 2003; Kim, D., et al., *Biosens. Bioelectron.* 20:69-74, 2004; Bandiera, L., et al., *Biosens Bioelectron* 22:2108-2114, 2007; Yan, F., et al., *Biosens. Bioelectron.* 24:1241-1245, 2009; Jagannathan, L., and Subramanian, V. *Biosens. Bioelectron.* 25:288-293, 2009; Fixe, F., et al., *Biosens. Bioelectron.* 21:888-893, 2005; Barbaro, M., et al., *IEEE Trans. Electron. Devices* 53:158-166, 2006; Barbaro, M., et al., *IEEE Electron. Device Lett.* 27:595-597, 2006; Zhang, G. J., et al., *Anal. Chim. Acta* 749:1-15, 2012; Chen, C.-P., et al., *Anal. Chem.* 83:1938-1943, 2011; Bunimovich, Y. L., et al., *J. Am. Chem. Soc.* 128:16323-16331, 2006; Li, Z., et al., *Nano Lett.* 245-247, 2004; Li, Z., et al., *Appl. Phys. A* 80:1257-1263, 2005; Hahm, J., et al., *Nano Lett.* 4:51-54, 2004; Zhang, G. J., et al., *Nano Lett.* 8:1066-1070, 2008; Zhang, G.-J., et al., *Biosens. Bioelectron.* 23:1701-1707, 2008; Zhang, G. J., et al., *Biosens. Bioelectron.* 23:1701-1707, 2009; Zhang, G. J., et al., *Sens. Actuators B Chem.* 146:138-144, 2010; Zhang, G. J., et al., *Biosens. Bioelectron.* 25:2447-2453, 2010; Gao, A., et al., *Nano Lett.* 12:5262-5268, 2012; Cai, B., et al., *ACS Nano* 8:2632-2638, 2014; Veigas, B., et al., *Biosens. Bioelectron.* 52:50-55, 2014; Wong, M. L., et al., *Biotechniques* 39:75-85, 2005; Branquinho, R., et al., *Biosens. Bioelectron.* 28:44-49, 2011; Toumazou, C., et al., *Nat. Methods* 10:641-646, 2013).

In some aspects, reagents for a life detection experiment (e.g., chemical(s), biochemical(s)) may be desiccated prior to use (e.g., storage during travel between celestial bodies), shielded from radiation (e.g., solar radiation, cosmic radiation, heavy ion radiation, neutron radiation, proton radiation, gamma radiation, beta radiation), or a combination thereof.

It is further contemplated that a life detection device may be evaluated in a terrestrial location (e.g., a volcanic site) where a low microbial density extremophile (e.g., extreme acidophile, a radiation resistant extremophile, a hyperpsychrophile) exists, to calibrate the device prior to use in an extraterrestrial location where an extremophile may also exist in relatively low abundance compared to a microbe rich terrestrial soil sample.

In many embodiments, it is contemplated that a sample of a celestial body will undergo one or more processes to separate one or more biomolecules from other biomolecule(s) and/or inorganic material(s) prior to a life detection experiment. For example, nucleic acid(s) may be extracted in microfluidic (e.g., a microfluidic chip), microchemostatic (e.g., microchemostat chip), electroelution, gel filtration, and/or gel (e.g., agarose gel) purification procedures to allow greater ease of detection by a nucleic acid detection device (Sadava et al., "Life: The Science of Biology," Ninth Edition, W.H. Freeman, p. 540, 2009). It is further contemplated that a sample of a celestial body may comprise a plurality of different organisms' nucleic acids (e.g., metagenomic nucleic acids), and the plurality of nucleic acid sequences may interfere with amplification, detection, and/or sequencing of specific nucleic acid sequence(s) (e.g., a single specie's nucleic acid sequence). In some aspects, the life detection equipment may comprise a microfluidic device, such as a microfluidic chip comprising nanoliter wells, though typical well sizes of 10-100 microliters may be used in some embodiments, with regents capable being used for life detection (e.g., nucleic acid detection, PCR, nucleic acid probes and/or a dye such as a fluorescent dye that promotes detection of a nucleic acid).

In some aspects, it is contemplated that nucleic acid sequence(s) conserved in terrestrial organisms (e.g., a 16S ribosomal microbial nucleic acid, a 18S ribosomal eukaryotic nucleic acid) may be selected for detection, because if extraterrestrial and terrestrial life have a common progenitor, a nucleic acid sequence conserved in terrestrial organisms may also be detected in an extraterrestrial (e.g., Martian) organism.

Example 17: Ancestor Analysis of Non-Terrestrial Organism(s)

Prokaryotes are by far the most numerous organisms on Earth. Two prokaryotic lineages diverged early in the history of life on Earth: bacteria and archaea. An early merging of these two groups is thought to have given rise to the eukaryotic lineage, including humans. Features in common between all living cells on Earth (e.g., glycolysis, DNA, similar genetic codes driving transcription and translation, semi-conservative DNA replication, plasma membranes and ribosomes abundantly present), support the conclusion that all living cells are related to one another on Earth. If life had multiple origins, there would be little reason to suspect all such cells to use overwhelmingly similar genetic codes or to share complicated structures as unique as ribosomes. Furthermore, similarities in DNA sequences of universal genes (such as those that encode the structural components of ribosomes) confirm the monophyly of Earth life.

Beginning at the origin of life on Earth, ancient prokaryotes existed until about 2-3 billion years ago, when the last common prokaryotic ancestor of all Earth species existed. During these same epochs, Mars was much wetter and warmer than it is today [D. C. Catling and C. Leovy, *Encylcopedia of the Solar System* (Ed. L. McFadden, P. Weissman), Academic Press, p. 301-314, 2006]. Thus, the conditions that existed on Earth that led to the abiogenesis of life also existed on Mars. Common ancestor's descendants then diverged into Bacteria (which further diverged into e.g., spirochetes, chlamydias, high G-C Gram positives, low G-C Gram positives, cyanobacteria, proteobacteria), and another branch that further split into the Euryarcheota and Archaea (which further diverged into e.g., Crenarchaeota, etc.) branches. Less is known about the Archaea because many of these microbes have never been actually seen or isolated. Many Archaea are only known from samples of their DNA from the environment.

Classification schemes ("phylogenetic trees") help identify microbes and to reveal evolutionary relationships. Analysis of nucleotide sequences of ribosomal RNA (rRNA) genes provide the best evidence of evolutionary relationships among prokaryotes, even so far as pointing at an in-common ancient ancestor. This is true for several reasons: rRNA is evolutionarily ancient, as it was found in the common ancestor of Earth microbes; no free-living organisms (thus excluding viruses, prions, etc.) lack rRNA, so rRNA genes can be compared throughout the "tree of life" on Earth; rRNA plays a critical role in translation in all living cells on Earth, so lateral transfer of rRNA genes among distantly related Earth species is unlikely; and rRNA has evolved slowly enough that gene sequences can be aligned and analyzed even among distantly related species. Therefore, it is contemplated that comparisons of rRNA genes, regardless of origin, stand the best chance of revealing the probable phylogenetic relationships of Earth microbes among themselves, and extra-terrestrial microbes among themselves, and possibly among extraterrestrial microbes and Earth microbes.

Numerous lines of evidence indicate that if Mars has extant life, it is likely to be methanogenic and/or magnetotactic (e.g., possessing magnetosomes). It is also likely to be similar in size to nano-bacteria on Earth (McKay et al., *Science*, 273 (5277):924-930, 1996). If so, and if they are similar in evolution to the same sort of microbes on Earth, it may be possible to place putative Mars microbes into phylogenetic trees based upon their rRNA sequences. For example, the photoautotrophic ancestor of proteobacteria further diverged (e.g., deltaproteobacteria, epsilonproteobacteria, alphaproteobacteria, betaproteobacteria, and gammaproteobacteria), to include photosynthetic (photoautotrophs) proteobacteria, as well as some groups becoming non-photosynthetic (e.g., chemolithotrophs; chemoheterotrophs) proteobacteria. Some species of Euryarchaeota share the property of producing methane ($CH_4$) by reducing carbon dioxide. Comparison of rRNA gene sequences has revealed a close evolutionary relationship among these methanogenic species. Judicious selection of rRNA sequences arising in such Euryarchaeota as probes for similar microbes on Earth is a most-probable path to identifying relationships between them and extraterrestrial DNA. Additionally, selection of primers to amplify nucleic acid sequences of microbial organisms similar to those on Earth associated with microbial gradients that are specifically associated with a particular type of ore (e.g., a precious metal, a petroleum deposit) may be used to prospect for useful minerals and/or resources either on Earth or an another celestial body.

It is relatively simple using techniques known by those of skill in the art of phylogenetic sequencing to design Polymerase Chain Reaction ("PCR") primers that will specifically amplify RNA sequences directly from heterogeneous mixtures of templates (Givannoni et al., *Nature*, 345(6270): 60-63, 1990; Amman et al., *Nature*, 351(6321):161-164, 1991; Fry et al., *FEMS Microbiol Lett.* 67(2):165-168, 1991; Fry et al., *J Gen Microbiol.* 137(5):1215-1222, 1991; "Bacterial Diversity and Systematics," Eds. Priest, Fergus, Ramos-Cormenzana, Alberto, Tindall, B. J., Springer, US, 1994.). PCR primers which specifically amplify rRNA primers which specifically amplify rRNA sequences from the Euryarchaeota, without concomitant amplification of similar but distinct microbial RNA (Embley et al., *FEMS Microbiol. Lett.*, 76(1-2):57-61, 1992). Using these primers it has been possible to identify methanogenic microbes without purifying DNA prior to amplification and PCR, even from very small numbers of microbial cells (e.g., 100-1000) (Embley et al., *J. Gen. Microbiol.*, 138(7):1479-1487, 1992; Embley et al., *FEMS Microbiol. Lett.*, 76(1-2):57-61, 1992; Finley et al., 1993). Once a sequence has been shown to belong to a methanogenic unknown microbe, its rRNA sequence can be compared to sequences form Earth Archaea and its phylogenetic relationships to Earth methanogens can be established (Larsen et al., *Nucleic Acids Res.* 21(13):3021-3023, 1993).

In one example, Earth Euryarchaeota derived rRNA gene probes are used to PCR sample(s) of Martian soil. If amplified DNA is detected, then the amplified DNA is sequenced, and the sequence of the amplified DNA (e.g., amplified rRNA gene sequence) is compared to the sequences of Earth Euryarchaeota. If the compared sequences are similar, but not the same or closely similar within the range of sequencing errors, then Martian microbes exist that share the evolutionary path with Earth microbes and the likely product of a shared abiogenesis as that of Earth (e.g., cross contamination between celestial bodies, panspermia origin of life, or other explanation for similarity). If the sequences are dissimilar, then Martian microbes exist, but are evolutionarily distinct from Earth microbes and therefore the product of a separate abiogenesis than that of Earth. In the occurrence that amplified DNA is not detected, then Martian microbes, if present and/or detected by other life detection experiment(s), are dissimilar (i.e., evolutionarily distinct) form Earth microbes. Any technique or apparatus known to those of skill in the art may be used to amplify, sequence, or analyze nucleic acids (see, for example, Green, M. R. and Sambrook, J. "Molecular Cloning: A Laboratory Manual (Fourth Edition)," Cold Spring Harbor Laboratory Press; 2012), though use of degenerate PCR primer probes, analysis of the efficiency of amplification of single PCR probe pairs as indicative of the degree of homology between an extraterrestrial nucleic acid sample and an Earth based microorganism, and use of compact apparatus for amplification, sequencing, and analysis is specifically contemplated (see, for example, Tian et al., *Nature*, 432: 1050-1054, 2004; Obeid et al., *Anal. Chem.*

75(2): 288-295, 2003; Paegel et al., *Current Opinion in Biotechnology*, 14(1): 42-50, 2003; Waters et al., *Anal. Chem.*, 70(1): 158-162, 1998; Lagally et al., *Anal. Chem.*, 73(3): 565-570, 2001; Tillib, S. V. and Mirzabekov, A. D., *Current Opinion in Biotechnology*, 12(1): 53-58, 2001; Ming-Hung Lee et al., *Lab on a Chip*, 3: 100-105, 2003; Zhang et al., *J. Am. Chem. Soc.*, 128(26): 8575-8580, 2006; and Tian et al., *Clinical Chemistry*, 47(2): 173-185, 2001).

Example 18: Reduction of Terrestrial Contamination Via Nuclease Coatings

It is contemplated that the results of any life detection experiment conducted using a penetrator system may be challenged by asserting that positive life detection results were false positive results produced by contaminating biomolecules from terrestrial organism(s) carried with the penetrator manufactured on Earth to a celestial body. To prevent such issues, it is contemplated that the penetrator may comprise a self-sterilizing coating that comprises one or more nucleases to degrade any contaminating nucleic acid(s) that may produce a false positive result in any life detection experiment involving the detection of a nucleic acid. In specific embodiments, such a nuclease may comprise an endonuclease, an exonuclease, a structure specific nuclease, a sequence specific nuclease, a flap endonuclease (e.g., a 5' nuclease), a meganuclease (e.g., an endodeoxyribonuclease), a deoxyribonuclease, a ribonuclease, or a combination thereof. Non-limiting examples of nucleases are shown below at Table 2, which lists the Enzyme Commission number ("EC No.") of the enzyme, the common name of the enzyme ("Enzyme"), the biochemical reaction catalyzed by the enzyme ("Enzyme Reaction"), the Chemical Abstracts Service Registry Number ("CAS No.") of the enzyme, and exemplary Protein Data Bank structural data entry number (s) ("PDB Entry No(s)") for nucleases known to those of ordinary skill in the art that may be used in the embodiments herein.

TABLE 2

Exemplary Nucleases

| EC No. | Enzyme | Enzymatic Reaction | CAS No. | PDB Entry No(s). |
|---|---|---|---|---|
| Examples of An Exodeoxyribonuclease producing 5'-phosphomonoester (EC 3.1.11) | | | | |
| 3.1.11.1 | exodeoxyribonuclease I | cleaves 3'- to 5'-producing a nucleoside 5'-phosphate | 9037-46-1 | 1fxx; 2qxf; 3c94; 3c95; 3hl8; 3hp9; 4hcb; 4hcc |
| 3.1.11.2 | exodeoxyribonuclease III | cleaves 3'- to 5'-producing nucleoside 5'-phosphates | 9037-44-9 | 1ako; 2ioc; 3a1j; 3w2y; 4b5f; 4ynq |
| 3.1.11.3 | exodeoxyribonuclease (lambda-induced) | cleaves 5'- to 3'-producing nucleoside 5'-phosphates | 37367-70-7 | 1avq; 3slp; 3sm4; 4wuz |
| 3.1.11.4 | exodeoxyribonuclease (phage SP3-induced) | cleaves 5'- to 3'-producing nucleoside 5'-phosphates | | |
| 3.1.11.5 | exodeoxyribonuclease V | ATP dependent cleavage 5'- to 3'- or 3'- to 5'- producing phosphooligonucleotides | 37350-26-8 5'- | 1w36; 3k70 |
| 3.1.11.6 | exodeoxyribonuclease VII | cleavage 5'- to 3'- or 3'- to 5'-producing nucleoside 5'-phosphates | 52933-20-7 | 1vp7 |
| Exodeoxyribonucleases Producing 3'-Phosphomonoesters (EC 3.1.12) | | | | |
| 3.1.12.1 | 5 to 3' exodeoxyribonuclease (nucleoside 3'-phosphate-forming) | cleaves 5'- to 3'-producing nucleoside 3'-phosphates | | |
| Exoribonucleases Producing 5'-Phosphomonoesters (EC 3.1.13) | | | | |
| 3.1.13.1 | exoribonuclease II | cleaves 3'- to 5'-producing nucleoside 5'-phosphates | 37288-24-7 | 1wlj; 2id0; 2ix0; 2ix1 |
| 3.1.13.2 | exoribonuclease H | exonucleolytically cleaves viral RNA-DA hybrid | | 1a30; 1b6k; 1wje; 2aoj; 2z54; 3bvb; 3vf7; 4qj9; 5agz; 6fiv; 7upj; 8hvp; 9hvp |
| 3.1.13.3 | oligonucleotidase | cleaves oligonucleotides producing nucleoside 5'-phosphates | 37288-23-6 | |
| 3.1.13.4 | poly(A)-specific ribonuclease | cleaves poly(A) to 5'-AMP | 110541-21-4 | 1ug8; 1whv; 2a1s; 2rok; 3ctr; 3ngq; 4b8a; 4czx; 4zkf |
| 3.1.13.5 | ribonuclease D | cleaves to remove residues at the 3'-terminus of tRNA producing 5'-mononucleotides | | 1yt3 |
| Exoribonucleases Producing 3'-Phosphomonoesters (EC 3.1.14) | | | | |
| 3.1.14.1 | yeast ribonuclease | cleaves producing nucleoside 3'-phosphates | | |

TABLE 2-continued

Exemplary Nucleases

| EC No. | Enzyme | Enzymatic Reaction | CAS No. | PDB Entry No(s). |
|---|---|---|---|---|
| Exonucleases Active with either Ribo- or Deoxyribonucleic Acids and Producing 5'-Phosphomonoesters (EC 3.1.15) | | | | |
| 3.1.15.1 | venom exonuclease | cleaves 3'- to 5'- producing nucleoside 5'-phosphates | 9025-82-5 | |
| Exonucleases Active with either Ribo- or Deoxyribonucleic Acids and Producing 3'-Phosphomonoesters (EC 3.1.16) | | | | |
| 3.1.16.1 | spleen exonuclease | cleaves 5'- to 3'-producing nucleoside 3'-phosphates | 9068-54-6 | |
| Endodeoxyribonucleases Producing 5'-Phosphomonoesters (EC 3.1.21) | | | | |
| 3.1.21.1 | deoxyribonuclease I | cleaves producing 5'-phosphodinucleotide and 5'-phosphooligonucleotide products | 9003-98-9 | 1emv; 1v15; 2a3z; 2g7e; 2xh3; 3dni; 3w3d; 4awn |
| 3.1.21.2 | deoxyribonuclease IV | cleaves apurinic/apyrimidinic ssDNA producing 5'-phosphooligonucleotide products | 63363-78-0 | 1fzr; 1xp3; 2nqh; 2x7w; 3aal; 3cae; 4hn0; 4k1g |
| 3.1.21.3 | type I site-specific deoxyribonuclease | ATP dependent cleavage of DNA producing double-stranded fragments having terminal 5'-phosphates | 37263-09-5 | 2w00; 2w74; 2y3t; 4be7; 4beb; 4bec |
| 3.1.21.4 | type II site-specific deoxyribonuclease | cleaves DNA producing specific double-stranded fragments having terminal 5'-phosphates | 9075-08-5 | 1az3; 1pvu ; 1yuv; 2aud; 2ixs; 2vla; 3a4k; 3e43; 3zi5; 4abt; 4rdm |
| 3.1.21.5 | type III site-specific deoxyribonuclease | cleaves DNA producing specific double-stranded fragments having terminal 5'-phosphates | 9075-08-5 | |
| 3.1.21.6 | CC-preferring endodeoxyribonuclease | CC sequence preferential cleavage producing 5'-phosphooligonucleotide products | 37211-67-9 | |
| 3.1.21.7 | deoxyribonuclease V | apurinic or apyrimidinic site cleavage producing a 5'-phosphate products | 61970-03-4 | 2w35; 3ga2; 3goc; 3hd0; 4b20; 4xpu |
| 3.1.21.8 | T$_4$ deoxyribonuclease II | nicks and cleaves dsDNA having cytosine | | |
| 3.1.21.9 | T$_4$ deoxyribonuclease IV | cleaves ssDNA at deoxycytidine's 5' phosphodiester bond of | | |
| Endodeoxyribonucleases Producing 3'-Phosphomonoesters (EC 3.1.22) | | | | |
| 3.1.22.1 | deoxyribonuclease II | cleaves producing nucleoside 3'-phosphates and 3'-phosphooligonucleotide products | 9025-64-3 | 1e7d; 1hh1; 1q8r; 2eo0; 2wcz; 2wj0; 4ep4; 4tkk |
| 3.1.22.2 | *Aspergillus* deoxyribonuclease K$_1$ | cleaves producing nucleoside 3'-phosphates and 3'-phosphooligonucleotide products | 264922-12-5 | |
| 3.1.22.4 | crossover junction endodeoxyribonuclease | cleavage at a DNA crossover junction (Holliday junction) | 99676-43-4 | |
| 3.1.22.5 | deoxyribonuclease X | cleaves supercoiled plasma DNA producing linear DNA duplexes | 97002-82-9 | |
| Site-Specific Endodeoxyribonucleases Specific for Altered Bases (EC 3.1.25) | | | | |
| 3.1.25.1 | deoxyribonuclease (pyrimidine dimer) | cleaves near pyrimidine dimers producing 5'-phosphate products | 66143-22-4 | 1eni; 1enk; 2end |
| Endoribonucleases Producing 5'-Phosphomonoesters (3.1.26) | | | | |
| 3.1.26.1 | *Physarum polycephalum* ribonuclease | cleaves producing 5'-phosphomonoester | 9001-99-4 | |
| 3.1.26.2 | ribonuclease alpha | cleaves producing 5'-phosphomonoester | | |
| 3.1.26.3 | ribonuclease III | cleaves producing a 5'-phosphomonoester | 9073-62-5 | 1i4s ; 1o0w; 1t4o ; 2a11; 2lup; 2qvw; 3c4b; 3o2r; 4m2z; 4ngb; 4oog; 4wyq |

TABLE 2-continued

Exemplary Nucleases

| EC No. | Enzyme | Enzymatic Reaction | CAS No. | PDB Entry No(s). |
|---|---|---|---|---|
| 3.1.26.4 | ribonuclease H | cleaves producing 5'-phosphomonoester | 9050-76-4 | 1a5v; 1zbf; 2b7f; 2e4l; 2zqb; 3aa2; 3vn5; 4bac; 4ztj |
| 3.1.26.5 | ribonuclease P | cleaves tRNA precursor to remove 5'-extranucleotides | 71427-00-4 | 1a6f; 1x0t; 2av5; 2zae; 3iab; 3wz0; 4g23; 4xgl; 4xgm |
| 3.1.26.6 | ribonuclease IV | cleaves poly(A) producing 3'-hydroxy and 5'-phosphate group terminated products | 61536-76-3 | |
| 3.1.26.7 | ribonuclease P4 | cleaves tRNA precursor to remove 3'-extranucleotides | 71427-00-4 | |
| 3.1.26.8 | ribonuclease M5 | cleaves 5S-rRNA precursor to remove twenty one 5'and forty two 3'termini nucleotides | 62253-00-3 | |
| 3.1.26.9 | ribonuclease [poly-(U)-specific] | cleaves poly(U) producing 3'-hydroxy and 5'-phosphate group terminated products | 54249-90-0 | |
| 3.1.26.10 | ribonuclease IX | cleaves poly(U) or poly(C) producing 3'-hydroxy and 5'-phosphate group terminated products | 9001-99-4 | |
| 3.1.26.11 | tRNase Z | cleaves precursor to tRNA removing 3 nucleotides to produce a 3'hydroxy group tRNA terminus | 98148-84-6 | 1ww1; 1y44; 2cbn; 2e7y; 3zwf; 4gcw |
| 3.1.26.12 | ribonuclease E | cleaves A- and U-rich regions in ssRNA | 76106-82-6 | 1slj ; 1smx; 1sn8; 2fym; 2vmk; 2vrt; 3h1c; 3h8a; 4oxp |
| 3.1.26.13 | retroviral ribonuclease H | Endolytically cleaves RNA at a RNA/DNA hybrid | | 1a30; 1tzt; 2a1e; 2zye; 3a2o; 3zpu; 4a6b; 4zls; 5agz; 5upj; 6fiv; 6upj; 7hvp; 7upj; 8hvp; 9hvp |

Endoribonucleases Producing 3'-Phosphomonoesters (EC 3.1.27)

| 3.1.27.1 | ribonuclease T$_2$ | cleaves producing nucleoside 3'-phosphates and 3'-phosphooligonucleotides | 37278-25-4 | 1bk7; 1ucc; 1vd3; 3d3z; 3t0o; 3u97 |
|---|---|---|---|---|
| 3.1.27.2 | Bacillus subtilis ribonuclease | cleaves producing 2',3'-cyclic nucleotides | | |
| 3.1.27.3 | ribonuclease T$_1$ | cleaves producing nucleoside 3'-phosphates and 3'-phosphooligonucleotides with Gp ends | 9026-12-4 | 1ay7; 1zgx; 2aad; 2xdd; 3a5e; 3wr2; 4bir; 4rnt; 5bir; 5rnt; 6gsp; 6rnt; 7gsp; 7rnt; 8rnt; 9rnt |
| 3.1.27.4 | ribonuclease U$_2$ | cleaves producing nucleoside 3'-phosphates and 3'-phosphooligonucleotides wth Ap or Gp ends | 37205-57-5 | 1rtu; 3agn; 3ago; 3ahs; 3ahw |
| 3.1.27.5 | pancreatic ribonuclease | cleaves producing nucleoside 3'-phosphates and 3'-phosphooligonucleotides with Cp or Up ends. | 9001-99-4 | 1lba; 1rha; 1z6s; 2aa5; 2zpo; 3a1r; 3tsr; 4ao1; 4ygw; 5e13; 5rsa; 6rat; 6rsa; 7rat; 7rsa; 8rat; 8rsa; 9rat; 9rsa |
| 3.1.27.6 | Enterobacter ribonuclease | cleaves producing nucleoside 3'-phosphates and 3'-phosphooligonucleotides | 395640-99-0 | 2ea1; 2pqx; 2pqy |
| 3.1.27.7 | ribonuclease F | cleaves RNA precursor to produce 5'-hydroxy and 3'-phosphate groups | 80498-18-6 | |
| 3.1.27.8 | ribonuclease V | cleaves poly(A) to produce oligoribonucleotides and 3'-AMP | 74505-36-5 | |
| 3.1.27.10 | rRNA endonuclease | Site specific cleavage at guanosine and adenosine linkage in rat ribosome 28S | 1407-48-3 | 1de3; 1r4y |

TABLE 2-continued

Exemplary Nucleases

| EC No. | Enzyme | Enzymatic Reaction | CAS No. | PDB Entry No(s). |
|---|---|---|---|---|
| Endoribonucleases Active with either Ribo- or Deoxyribonucleic Acids and Producing 5'-Phosphomonoesters (EC 3.1.30) | | | | |
| 3.1.30.1 | *Aspergillus* nuclease $S_1$ | cleaves producing 5'-phosphomononucleotide and 5'-phosphooligonucleotide products | 37288-25-8 | 1ak0; 3w52; 4cwm; 4cxo; 4cxp; 4cxv |
| 3.1.30.2 | *Serratia marcescens* nuclease | cleaves producing 5'-phosphomononucleotide and 5'-phosphooligonucleotide products | 9025-65-4 | 1g8t; 1qae; 1ql0; 1smn; 4e3y |
| Endoribonucleases Active with either Ribo- or Deoxyribonucleic Acids and Producing 3'-Phosphomonoesters (EC 3.1.31) | | | | |
| 3.1.31.1 | micrococcal nuclease | cleaves producing nucleoside 3'-phosphates and 3'-phosphooligonucleotide products | 9013-53-0 | 1a2t; 1u9r; 2enb; 2sob; 3bdc; 3va5; 4df7; 4zuj; 5c3w; 5nuc |

All patents, published patent applications and other publications cited herein are hereby incorporated herein by reference to the extent that they describe materials and methods supplementary to that set forth herein. One skilled in the art will readily appreciate that the present invention is well adapted to carry out any objects and obtain the ends and advantages mentioned as well as those inherent therein. The preferred compositions and methods described herein are exemplary and intended to be representative of other embodiments which will be apparent to those skilled in the art in light of the present disclosure. For instance, in light of the present disclosure and representative examples, changes in the disclosed apparatus, devices, compositions and methods and other uses will occur to those skilled in the respective arts of preparing and using spacecraft, scientific equipment, robotics, paints and coatings which are encompassed within the spirit of the invention and defined by the scope of the appended claims. The present examples, therefore, are not to be considered as limiting the scope of the present invention.

What is claimed is:

1. A probe for penetrating surface material of a celestial body, comprising, a penetrator, wherein the penetrator comprises:
   a plurality of body sections;
      an equipment payload, wherein the equipment payload is housed within at least one of the body sections, wherein the equipment payload comprises
         a scientific equipment package, wherein the scientific equipment package comprises
            at least one piece of scientific equipment, wherein the at least one piece of scientific equipment is configured to detect at the celestial body at least one of a nucleic acid and metabolism of a living cell as part of a life detection experiment, wherein the celestial body is an extraterrestrial body with respect to a terrestrial body at which the probe is manufactured; and
         a sampling device, wherein the sampling device is configured to obtain material of the celestial body and move the material to the piece of scientific equipment to undergo the life detection of at least one of a nucleic acid and metabolism of a living cell;
      an antimicrobial and anti-nucleic acid coating, wherein the antimicrobial and anti-nucleic acid coating is applied to an internal surface of the penetrator to promote biological sterility and reduce nucleic acid contamination prior to conducting the life detection experiment to improve data quality of the life detection experiment, wherein the antimicrobial and anti-nucleic acid coating comprises at least one of a nuclease and an antimicrobial biomolecule to enable degradation of at least one of a contaminating nucleic acid and a contaminating living cell imparted upon the penetrator at the terrestrial body that may produce a false positive result in the life detection experiment during said detection of the at least one of the nucleic acid and the metabolism of the living cell;
      a communication device operatively connected to the piece of scientific equipment to electromagnetically transmit the results of the life detection experiment;
      a microprocessor operatively associated with at least one of the scientific equipment package and the communication device; and
   an electrical power system operatively associated with at least one of the scientific equipment package, the communication device, and the microprocessor, wherein the power system comprises a battery.

2. The scientific probe for penetrating surface material of a celestial body of claim 1, wherein the communication package electromagnetically transmit the results of the life detection experiment to a communication network, wherein the communication network comprises
   at least one selected from a ground based relay, an atmosphere borne relay, a space based relay, and an Earth based satellite dish, wherein the ground based relay comprises at least one selected from a lander and another penetrator,
   wherein the atmosphere borne relay comprises
      at least one selected from a balloon, a drone, and a sub-orbital craft, and wherein the space based relay comprises at least one selected from a satellite, and an orbiting spacecraft.

3. The scientific probe for penetrating surface material of a celestial body of claim 1, wherein the scientific equipment package comprises at least one additional piece of equipment configured to detect life, measure ground movements, measure thermal levels, or determine size and shape of the celestial body and exact positions of points on its surface and with description of variations of its gravity field.

4. The scientific probe for penetrating surface material of a celestial body of claim 1, wherein the communication device comprises a plurality of communication devices.

5. The scientific probe for penetrating surface material of a celestial body of claim 1, wherein the electrical power system further comprises at least one of a solar panel, a thermoelectric generator, and a windmill.

6. The scientific probe for penetrating surface material of a celestial body of claim 1, wherein the penetrator comprises a depth achievement device, wherein the depth achievement device comprises:
at least one explosive charge operatively associated with a forward body section of the penetrator that detonates upon or after impact of the penetrator with the celestial body's surface, a drill operatively associated with the forward body section of the penetrator, another penetrator that impacts the same location of the surface of the celestial body prior to impact of the penetrator, and a bomb that impacts and detonates at the same location of the surface of the celestial body prior to impact of the penetrator.

7. The scientific probe for penetrating surface material of a celestial body of claim 1, wherein the penetrator further comprises an outer aeroshell to protect the penetrator during atmospheric entry.

8. The scientific probe for penetrating surface material of a celestial body of claim 1, wherein the penetrator comprises an engine, wherein the engine comprises:
at least one selected from a rocket engine and a jet engine, wherein the engine begins to function at or after release from the spacecraft to move the penetrator to a selected area of surface material of the celestial body to impact, to prevent impact of the penetrator with the surface material of a celestial body at a speed below about 290 kilometers per hour, to function as a depth achievement device at or after impact, or a combination thereof.

9. The scientific probe for penetrating surface material of a celestial body of claim 1, wherein the penetrator comprises a descent speed control device to prevent impact of the penetrator with the surface material of a celestial body at a speed in excess of about 1450 kilometers per hour, wherein the descent speed control device comprises at least one selected from a parachute, a rocket engine, and a jet engine.

10. The scientific probe for penetrating surface material of a celestial body of claim 1, wherein penetrator probe targets the surface material of the celestial body impacted by the penetrator probe, wherein the targeted surface material is at least one selected from a lava tube, a cave, a karst, a crater gully, a steep inclined area, or a subsurface deposit of at least one selected from water, oil, a mineral, or an ore.

11. The scientific probe for penetrating surface material of a celestial body of claim 1, wherein the penetrator is a plurality of penetrators.

12. The scientific probe for penetrating surface material of a celestial body of claim 11, wherein the plurality of penetrators are designed to impact different locations of surface material of the celestial body, wherein at least one penetrator of the plurality of penetrators comprise at least one of a different shape, different hardened material, and different depth achievement device, and different impact damper relative to another penetrator of the plurality of penetrators.

13. A scientific probe for penetrating surface material of a celestial body with a penetrator, wherein the penetrator comprises:
a forward-body section, a mid-body section, and an aft-body section,
wherein the forward-body section has a shape and hardened material surface conducive to penetrating the surface of a celestial body between about 0.5 meters to about 10 meters upon an impact speed of about 290 kilometers per hour to about 1450 kilometers per hour, wherein the shape is at least one selected from a screw shape, a needle shape, a rounded shape, a pointed shape, and a dart shape, wherein the hardened material comprises at least one material selected from diamond, tungsten, and tungsten carbide,
wherein the mid-body section has a generally cylindrical shape to promote aerodynamic motion of the forward-body section toward a celestial body's surface prior to impact,
wherein the aft-body section comprises at least one aerodynamic fin to promote aerodynamic motion of the forward-body section toward a celestial body's surface prior to impact, and
wherein the length of the penetrator prior to contact with the surface of the celestial body is between about 0.15 meters to about 6 meters;
an equipment payload, wherein the equipment payload is housed within at least one of the forward-body section, the mid-body section, and the aft-body section, wherein the equipment payload comprises,
a scientific equipment package, wherein the scientific equipment package comprises,
at least one piece of scientific equipment, wherein the at least one piece of scientific equipment is configured to detect at the celestial body at least one of a nucleic acid and metabolism of a living cell as part of a life detection experiment, wherein the celestial body is an extraterrestrial body with respect to a terrestrial body at which the probe is manufactured;
a sampling device, wherein the sampling device is configured to obtain material of the celestial body and move the material to the piece of scientific equipment to undergo the detection of at least one of a nucleic acid and metabolism of a living cell;
an impact damper to reduce impact damage to other parts of the equipment payload, wherein the impact damper is at least one selected from an air-bag device, a spring, and a shock absorber,
a communication device operatively connected to the piece of scientific equipment to electromagnetically transmit the results of the life detection experiment, wherein the communication device comprises,
a radio transmitter,
an antenna capable of electromagnetically transmitting the results of the life detection experiment,
the umbilical wire connecting the mid-body section to the aft-body section, wherein the umbilical wire is operatively associated with the at least one of the scientific equipment package and the antenna;

a microprocessor operatively associated with at least one of the scientific equipment package and the communication device;

an electrical power system operatively associated with at least one of the scientific equipment package, the communication device, and the microprocessor, wherein the power system comprises a battery; and wherein the penetrator is capable of being operatively associated with a spacecraft, wherein the spacecraft positions the penetrator above the surface material of celestial body and then the penetrator is released so to impact the surface material of the celestial body, wherein the penetrator comprises:

an antimicrobial and anti-nucleic acid coating, wherein the antimicrobial and anti-nucleic acid coating is applied to an internal surface of the penetrator to promote biological sterility and reduce nucleic acid contamination prior to conducting the life detection experiment to improve data quality of the life detection experiment, wherein the antimicrobial and anti-nucleic acid coating comprises at least one of a nuclease and an antimicrobial biomolecule to enable degradation of at least one of a contaminating nucleic acid and a contaminating living cell imparted upon the penetrator at the terrestrial body that may produce a false positive result in the life detection experiment during said seeking to detect the at least one of the nucleic acid and the metabolism of the living cell, wherein the penetrator penetrates about 1 meter to about 10 meters deep in a celestial body to allow the sampling device to obtain material of the celestial body from at least 1 meter below the surface of the celestial body prior to conducting the life detection experiment, wherein the antenna is operatively associated with the aft-body section, and wherein the aft-body section separates from the mid-body section upon penetration of the mid-body section into the surface of the celestial body due to the aerodynamic fin impeding penetration of the aft-body section upon contact with the surface of the celestial body so the antenna is located above, at or near the surface of the celestial body upon rest after contact with the surface of the celestial body to promote transmission of the results of the life detection experiment.

14. A method for penetrating surface material of a celestial body, comprising:

assembling a penetrator that comprises a forward-body section, a mid-body section, and an aft-body section, wherein the forward-body section has a shape and hardened material surface conducive to penetrating the surface of a celestial body between about 0.5 meters to about 10 meters upon an impact speed of about 290 kilometers per hour to about 1450 kilometers per hour, wherein the shape is at least one selected from a screw shape, a needle shape, a rounded shape, a pointed shape, and a dart shape, wherein the hardened material comprises at least one material selected from diamond, tungsten, and tungsten carbide, wherein the mid-body section has a generally cylindrical shape to promote aerodynamic motion of the forward-body section toward a celestial body's surface prior to impact, wherein the aft-body section comprises at least one aerodynamic fin to promote aerodynamic motion of the forward-body section toward a celestial body's surface at an angle between about 90 degrees perpendicular to about 45 degrees to the celestial body's surface prior to impact to promote penetration upon impact with the celestial body's surface, wherein the aft-body section separates from the mid-body section upon penetration of the mid-body section into the surface of the celestial body due to the aerodynamic fin impeding penetration of the aft-body section upon contact with the surface of the celestial body so part or all of the aft-body section is located above, at or near the surface of the celestial body upon the end of impact driven forward motion after contact with the surface of the celestial body, and wherein the length of the penetrator prior to contact with the surface of the celestial body is between about 0.15 meters to about 6 meters;

incorporating into the penetrator an equipment payload, wherein the equipment payload is housed within at least one of the forward-body section, the mid-body section, and the aft-body section, wherein the equipment payload comprises, an impact damper to reduce impact damage to other parts of the equipment payload, wherein the impact damper is at least one selected from an air-bag device, a spring, and a shock absorber, a scientific equipment package, wherein the scientific equipment package comprises, at least one piece of scientific equipment, wherein the at least one piece of scientific equipment is configured to detect at the celestial body at least one of a nucleic acid and metabolism of a living cell as part of a life detection experiment, wherein the celestial body is an extraterrestrial body with respect to a terrestrial body at which the probe is manufacture;

a sampling device, wherein the sampling device is configured to obtain material of the celestial body and move the material to the piece of scientific equipment to undergo the life detection of at least one of a nucleic acid and metabolism of a living cell, and wherein the sampling device accesses the material of the celestial body through an opening in a housing of the penetrator between the mid-body section and the aft-body section created by the separation of those sections after impact with the celestial body's surface;

an antimicrobial and anti-nucleic acid coating, wherein the antimicrobial and anti-nucleic acid coating is applied to an internal surface of the penetrator to promote biological sterility and reduce nucleic acid contamination prior to conducting the life detection experiment to improve data quality of the life detection experiment, wherein the antimicrobial and anti-nucleic acid coating comprises at least one of a nuclease and an antimicrobial biomolecule to enable degradation of at least one of a contaminating nucleic acid and a contaminating living cell imparted upon the penetrator at the terrestrial body that may produce a false positive result in the life detection experiment during said seeking to detect the at least one of the nucleic acid and the metabolism of the living cell, a communication device operatively connected to the piece of scientific equipment to electromagnetically transmit the results of the life detection experiment,
wherein the communication device comprises,
a radio transmitter,
an antenna capable of electromagnetically transmitting the results of the life detection experiment, wherein the antenna is operatively associated with the aft-body section so the antenna is located above, at or near the surface of the celestial body upon rest after contact with the surface of the celestial body to promote transmission of the results of the life detection experiment,
the umbilical wire connecting the mid-body section to the aft-body section, wherein the umbilical wire is operatively associated with the at least one of the scientific equipment package and the antenna;
a microprocessor operatively associated with at least one of the scientific equipment package and the communication device;
an electrical power system operatively associated with at least one of the scientific equipment package, the communication device, and the microprocessor, wherein the power system comprises a battery; and
wherein the penetrator is capable of being operatively associated with a spacecraft, wherein the spacecraft positions the penetrator above the surface material of celestial body and then the penetrator is released so to impact the surface material of the celestial body and penetrate about 1 meter to about 10 meters deep in the celestial body to allow the sampling device to obtain material of the celestial body from at least 1 meter below the surface of the celestial body prior to conducting the life detection experiment.

\* \* \* \* \*